United States Patent
Lee et al.

(10) Patent No.: US 8,738,135 B1
(45) Date of Patent: May 27, 2014

(54) REDUNDANT WIRES AND CONNECTORS FOR DBS AND HEART PACEMAKER ELECTRICAL STIMULATING DEVICE IMPLANTED IN ANIMALS

(71) Applicants: Chong Il Lee, Stanton, CA (US); Sergio Lara Pereira Monteiro, Los Angeles, CA (US)

(72) Inventors: Chong Il Lee, Stanton, CA (US); Sergio Lara Pereira Monteiro, Los Angeles, CA (US)

( * ) Notice: Subject to any disclaimer, the term of this patent is extended or adjusted under 35 U.S.C. 154(b) by 0 days.

(21) Appl. No.: 14/027,196

(22) Filed: Sep. 14, 2013

Related U.S. Application Data

(62) Division of application No. 12/586,763, filed on Sep. 28, 2009, now Pat. No. 8,565,868.

(60) Provisional application No. 61/194,515, filed on Sep. 29, 2008, provisional application No. 61/198,029, filed on Nov. 3, 2008.

(51) Int. Cl.
  *A61N 1/372* (2006.01)
  *A61N 1/375* (2006.01)
  *A61N 1/05* (2006.01)

(52) U.S. Cl.
  CPC ............ *A61N 1/3754* (2013.01); *A61N 1/3752* (2013.01); *A61N 1/056* (2013.01)
  USPC .............................. 607/37; 607/122; 607/115

(58) Field of Classification Search
  CPC ... A61N 1/3752; A61N 1/3754; A61N 1/056; A61N 2001/0585
  USPC ............................................. 607/37, 122, 115
  See application file for complete search history.

(56) References Cited

U.S. PATENT DOCUMENTS

| | | | |
|---|---|---|---|
| 7,571,010 B2 * | 8/2009 | Zarembo et al. | 607/115 |
| 7,660,635 B1 * | 2/2010 | Verness et al. | 607/122 |
| 8,297,997 B2 | 10/2012 | Martens | |
| 8,509,872 B2 | 8/2013 | Lee et al. | |
| 2005/0015133 A1 * | 1/2005 | Ibrahim et al. | 607/137 |
| 2010/0030298 A1 | 2/2010 | Martens | |

FOREIGN PATENT DOCUMENTS

EP  20090759814  10/2011

* cited by examiner

*Primary Examiner* — Christopher D Koharski
*Assistant Examiner* — Michael Carey

(57) ABSTRACT

A method and a system to increase the reliability of the electrical connections between the electrodes and the battery/controlling electronics of an electrical stimulating device as DBS (Deep Brain Stimulator), heart pacemakers and the like. We disclose a redundant connector which in prior art is used to complete the connection between the wires leading to the electrodes and the wires leading to the battery/controlling electronics, which is subject to loss of continuity due to the adverse effect of body fluids, and a set of redundant wires from this redundant connector to the battery/controlling electronics, which often breaks, due to repeated motion by the human subject, particularly in the DBS case, where the wires run down the neck of the human subject.

8 Claims, 18 Drawing Sheets

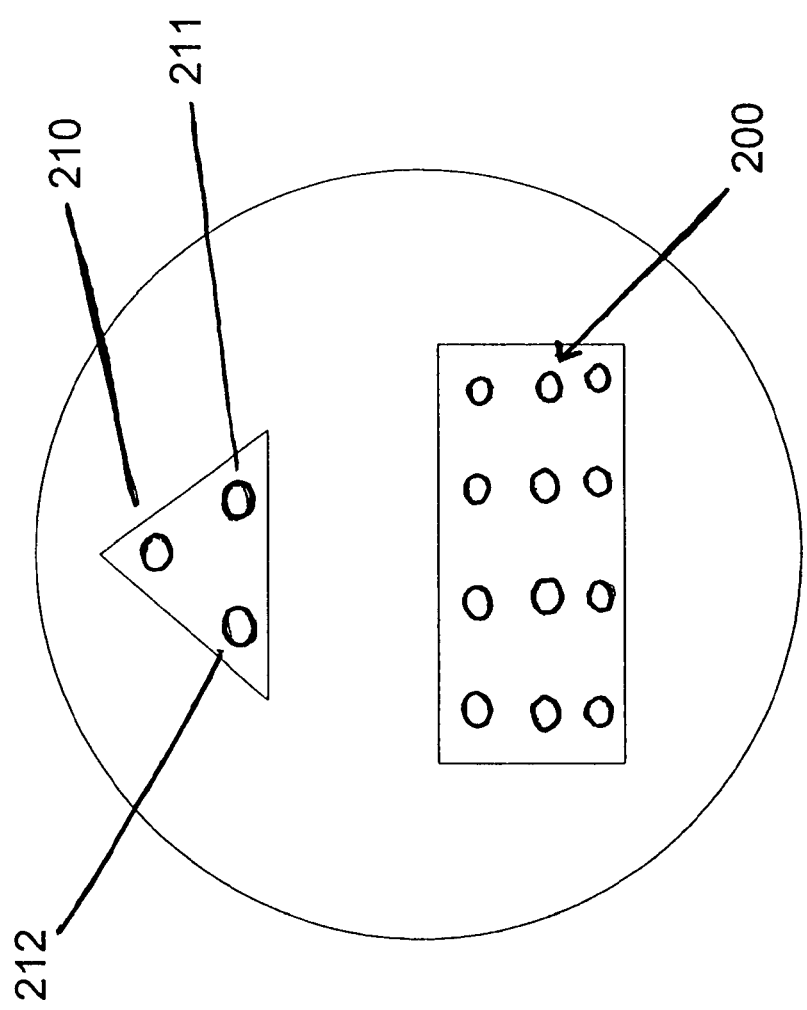

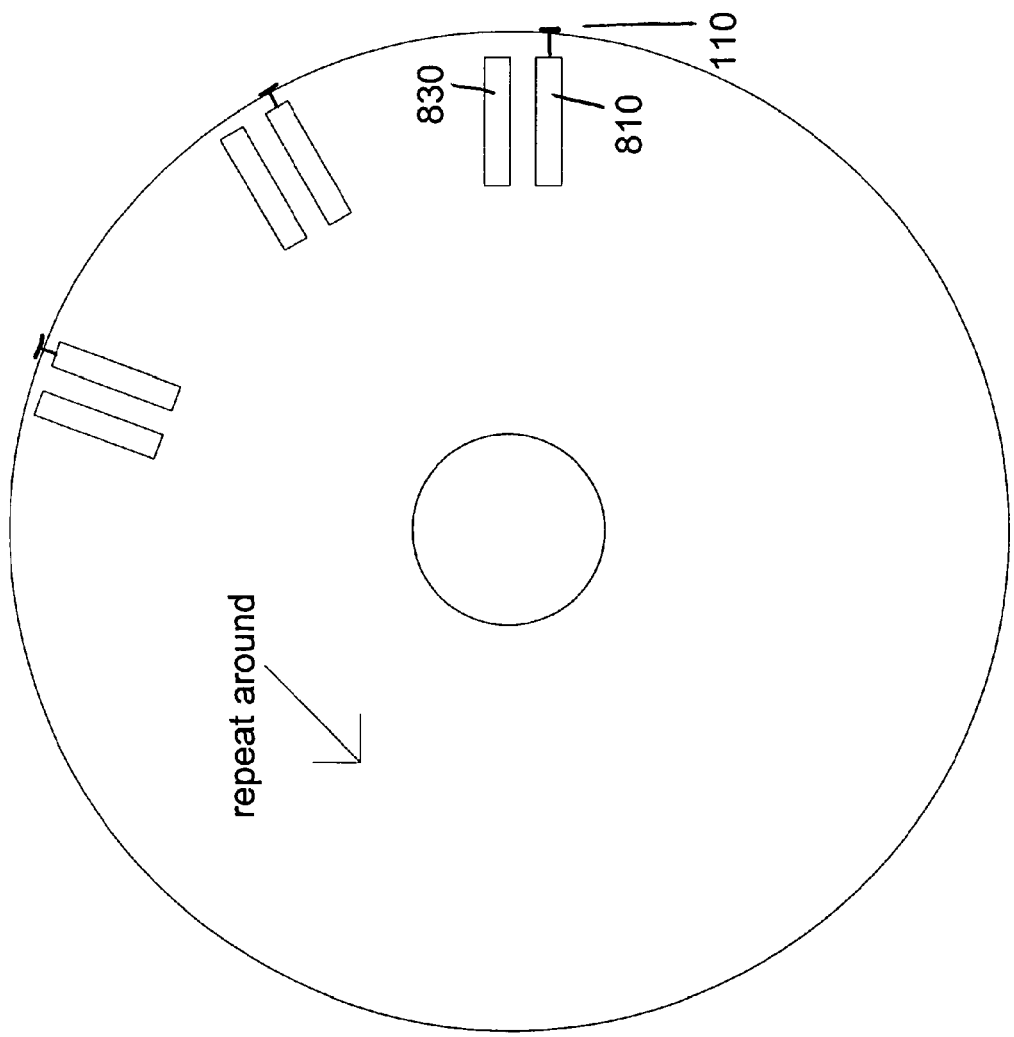

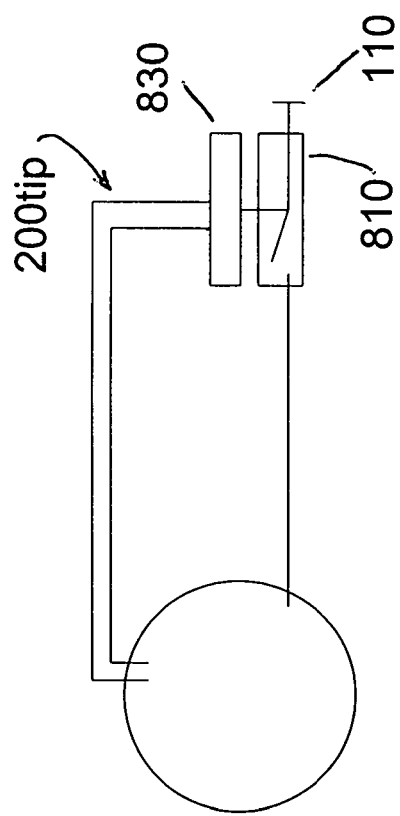

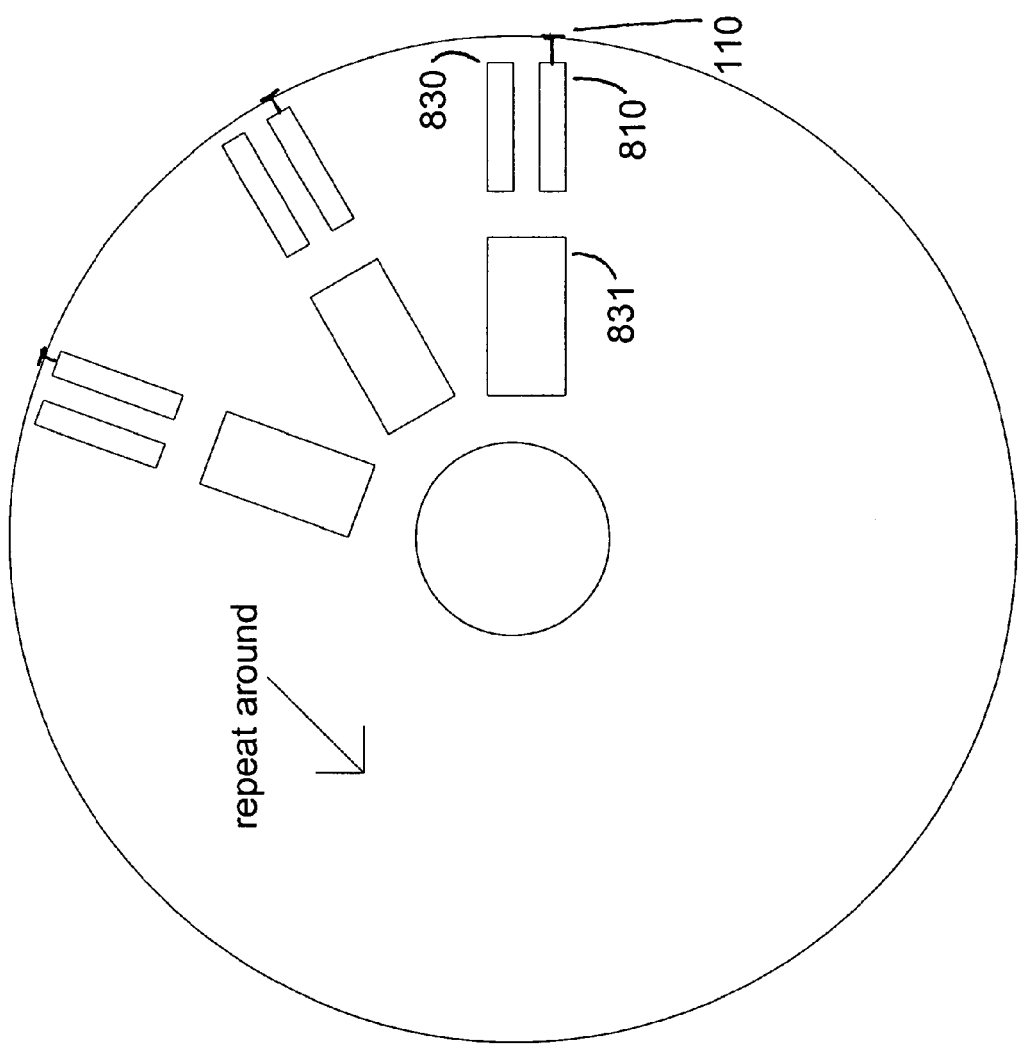

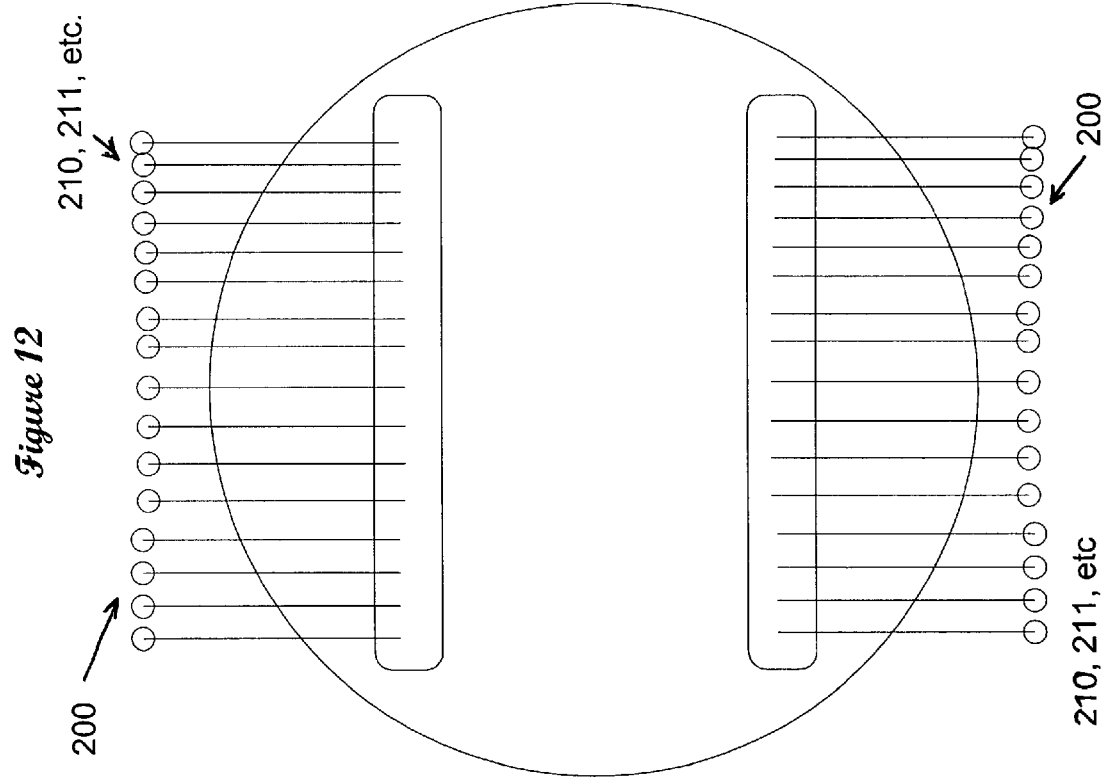

REDUNDANT WIRES AND CONNECTORS FOR DBS AND HEART PACEMAKER ELECTRICAL STIMULATING DEVICE IMPLANTED IN ANIMALS

CROSS REFERENCES TO RELATED APPLICATIONS

This application is a continuation of application Ser. No. 12/586,763, filed Sep. 28, 2009, published number US-2010-0082076 A1, now issued U.S. Pat. No. 8,565,868 issued on Oct. 22, 2013, which claims the benefit of U.S. Provisional Application No. 61/198,029, filed Nov. 3, 2008, and provisional application No. 61/194,515, filed Sep. 29, 2008. This application is also related to issued U.S. Pat. No. 8,335,551, issued on Dec. 18, 2012 and to issued U.S. Pat. No. 8,509,872, issued Aug. 13, 2013. All these share the same present inventors and are incorporated here in their entirety by reference.

BACKGROUND OF THE INVENTION

Field of Invention

This invention relates to cellular electrical stimulation in general, for animals, including humans, and neuron electrical stimulation in particular.

Field of Invention

This invention relates to cell electrical stimulators and reading probes for animals, including humans, in general, and brain electrical stimulators and reading probes in particular.

Short Introduction to the Art

It is well established that the neuron signals are electrical propagating signals. The roots of this fact can be traced at least to the Italian Luigi Galvani as early as 1771 with his famous frog's leg experiment. Electrically stimulating neurons that carry orders to muscles, or electrically stimulating the muscles directly, can therefore cause the muscles to contract or relax. It follows that the spinal cord and the whole brain, being as they are a collection of neurons, are electrical devices, the function of which could be expected to be affected if electrical currents were forced on them by some external agent.

Focusing attention now on the brain, it has been established that different brain functions occur in different parts of it, though some parts of the brain are known to be shared by more than one function. The French Paul Broca is credited with the first unequivocal evidence that the brain is segmented in areas with specialized functions (brain workers say "area" for what is actually a volume, a particular three dimensional part of the brain, practice that I will follow here, occasionally calling the attention of the reader to this misuse of the word). Paul Broca proved that speech is processed and controlled at a small area (that is, a volume) today known as the "Broca area" which is located in the left frontal lobe. Today the parts of the brain that are associated with speech, or with vision, or with the motion of the hand or with the motion of the big toe on the left foot, an so on, are all known; the brain is all mapped, as known in the trade. Eric R. Kandel (Eric R. Kandel, James H. Schwartz, and Thomas M. Jessell "Principles of Neural Science" $4^{th}$ edition (2000)) gives a good overview of the current state of the art from the academic point-of-view.

It follows from these two facts that electrical stimulation of any particular area of the brain (that is, a volume) should affect the function that depends on this area: speech, vision, motor, etc. This was indeed experimentally determined to be true, and eventually brain electrical stimulators were developed to affect parts that became dysfunctional. Brain stimulation to correct for motor disorders is the most common clinical application today, but stimulation can also cause emotions when it happens in the area that is associated with them. Similarly, stimulation of nerves that carry information from the body to be brain can stop (or cause) pain, and electrically stimulating the heart can keep it at the correct pace, or even to restart it when it happens to stop, as is done with pacemakers and defribilators. Electrically stimulating neurons that carry orders to muscles, or electrically stimulating the muscles directly, can therefore cause the muscles to contract or relax. This is what is achieved with heart pacemakers and heart defibrillators. A pacemaker could, in principle work stimulating the part of the brain that starts the process (assuming it is not autonomous), but this would be more complicated than stimulating the heart directly, so pacemakers are designed to affect the heart directly, and not the origin of the signal.

Leaving aside the mechanisms that underlie the result of electrical stimulation, which are not well known in all cases, it is possible today to use direct electrical stimulators to modify motor malfunctions as Parkinson's disease, essential tremor or epilepsy, or mood states as depression, or complex syndromes as eating disorders. Said brain electrical stimulation is achieved with electrodes permanently implanted in the desired part of the brain, which are connected to the necessary electrical power source (batteries or the like) and electronic circuitry to generate the appropriate electrical pulse. Severe diseases as Parkinson's disease are now treatable and often totally or largely curable, or at least substantially controlled, with direct electrical stimulation to the appropriate part of the brain. For Parkinson's disease stimulation, the device is one of a class generally known as Deep Brain Stimulators (DBS), because all the known parts of the brain that receive electrical stimulation to counter Parkinson's disease are located deep inside it, as the thalamus, the subthalamic nucleus (STN), the basal ganglia, or internal globus pallidus (GPi) the internal capsule and the nucleus accumbens. The electrical pulse for DBS is AC (alternate current) at f=~180 Hz (or 5.56 milliseconds between pulses), each pulse lasting approximately 90 microseconds (pulsewidth). The voltage depends on the patient, varying from as low as 2.5 V to as high as 5 V (all values approximate, varying between patients and also with time on the same patient). A separate class of stimulators are the superficial brain stimulators, known as cortical stimulators, that stimulate the brain cortex, which could also use the invention disclosed in this patent application with appropriate adaptations, largely on the geometry of the stimultor. There are also spinal stimulators, that stimulate the nerves at the spinal column, and other parts of the body, generally for pain control, but also for other problems. There are heart stimulators or pacemakers and also heart defribilators. These latter, heart pacemakers and defribilators, differ much from the device disclosed as the main embodiment of this patent application, but the same core principle disclosed in this invention, the method and means of more precisely applying the stimulation, and of shaping the electric field, so as to guide the current, apply to them too. Another application is artificial muscle stimulation, where artificial materials capable of contraction or distention when receiving the appropriate signal are used as artificial muscles. Another class of devices is composed of measuring probes, designed to measure the voltage (or current) in the brain or other body parts. All these variations can incorporate the system and method disclosed here to allow the use of a very large number of electrical contacts for stimulation or for measurement.

Discussion of Prior Art

The success of DBS to ameliorate Parkinson's disease symptoms is known in the medical community, particularly among neurosurgeons. Yet, many forms of Parkinson's diseases and other movement disorders too, are either unresponsive or only partially ameliorated by DBS (Michael S. Okun et al. "Multiple lead method for deep brain stimulation" A61N 1/00 International Application No.: PCT/US2005/033730 University of Florida Research Foundation, Inc.-30.03.2006). It is unknown the causes of the differences, but one of the speculations is not optimal positioning of the stimulating electrode, which would, as expected, fail to have optimal effect in this case due to failure to stimulate the chosen area. Benabid (A. L. Benabid, et al., *Stereotact Funct Neurosurg*, 62(1-4):76-84 (1994)) and Benabid (A. L. Benabid, et al., *J Neurol,*. 248 Suppl 3: 11137-47 (2001)) discuss this problem and others. Additionally, the success of DBS procedures can diminish over time. This deleterious effect is discussed by M. C. Kim et al. (M. C. Kim, B C Son, Y Miyagi, J-K Kang, "Vim thalamotomy for Holmes' tremor secondary to midbrain tumour" *J Neurol Neurosurg Psychiatry,* 73:453-455 (2002)). This latter decrease in efficacy of DBS is thought by some neurosurgeons to arise from motion of the implant inside the brain due to occasional sudden head movements, particularly due to a falling but also other causes. Our invention allow for correction of these deleterious factors.

Known side effects from brain stimulators caused it to be recognized the need for smaller electrode area for neural stimulation, but since nobody has been able to precisely position the stimulator in the brain, the only option has been to stimulate an area that is likely to be larger than necessary. This has been a widely known problem in the art of brain stimulators: unwanted side effects, as mood changes, uncontrolled motion of other muscles not intended to be affected, etc.

In "Detailed description", section A-1 Andrew Firlik et al. (Andrew Firlik et al. "Methods and apparatus for effectuating a lasting change in a neural-function of a patient" U.S. Pat. No. 7,577,481 (Aug. 18, 2009)) states that "The method 100 includes a diagnostic procedure 102 involving identifying a stimulation site at a location of the brain where an intended neural activity related to the neural-function is present.", which indicates that these inventors are aware of the need to identify a location of the brain where to apply stimulation. Yet their device assumes that the implant is indeed positioned at the desired target location, which the neurosurgeons know to be a very difficult task. Indeed, the difficulty of this task is indicated by the acceptance by the neurosurgeon community of the side effects, which arises from incorrect positioning of the stimulating device, which then applies electrical current also into undesired areas, thereby causing the known side effects. Our device offers a great latitude of the electrical stimulation point, thereby solving this problem. Moreover, Firlik et al. (Andrew Firlik et al. "Methods and apparatus for effectuating a lasting change in a neural-function of a patient" U.S. Pat. No. 7,577,481 (Aug. 18, 2009)) disclose an innovative application of their invention, which is to use electrical stimulation during physical therapy designed to readapt the brain of patients that have suffered some form of brain loss, either from a stroke, a car accident or the like. Such an application would require an adjustment of the stimulation site, which is difficult to achieve with the device they disclose, while the device we disclose in our invention is more suitable for readjusting the point of application of the electrical stimulation.

Wiler at al. (Allen Wyler and Brad Fowler, "Systems and methods for selecting stimulation sites and applying treatment, including treatment of symptoms of Parkinson's disease, other movement disorders, and/or drug side effects" U.S. Pat. No. 7,565,200 (Jul. 21, 2009)) At the end of the background section, the inventors acknowledge that: "Because MCS involves the application of stimulation signals to surface regions of the brain rather than deep neural structures, electrode implantation procedures for MCS are significantly less invasive and time consuming than those for DBS. As a result, MCS may be a safer and simpler alternative to DBS for treating PD symptoms. Present MCS techniques, however, fail to address or adequately consider a variety of factors that may enhance or optimize the extent to which a patient experiences short term and/or long term relief from PD symptoms." Which is likely to be a consequence that their invention is unable to precisely adjust the point of application of electrical stimulation, which is exactly the solution proposed by our invention. It is apparent, therefore, that the need for precisely pinpointing the location of application of the electrical stimulation is known in the art, at the same time that its solution has evaded solution.

Anne Pianca (Anne Pianca, "System for permanent electrode placement utilizing microelectrode recording methods" U.S. Pat. No. 7,177,701 (Feb. 13, 2007)) discloses a DBS system that works in association with a separate measuring electrode which aids in the location of the optimal placement of the DBS device. Yet Pianca's invention suffers from the disadvantage of increased trauma to the patient due to multiple insertions and withdraws of invasive instruments in the brain. A better solution would avoid such traumatic repetitive insertions. Our invention provide such improvement.

Benjamin Pless (Benjamim Pless et al. "Seizure sensing and detection using an implantable device", U.S. Pat. No. 6,810,285, (Oct. 26, 2004)) also describes a device that reads the waveforms produced by the brain, similarly to a EKG, and acts on these measurements, under the control of a microcomputer or similar device, to inject electrical current in the brain to forestall such symptoms as epileptic seizures. Pless device again fails to teach any means to precisely measure and to precisely insert the electrical corrective pulse.

Potential movement of the device, as well as other characteristics, are also disclosed in another US patent by Carl Wahlstrand (Carl Wahlstrand et al. "Reducing relative intermodule motion in a modular implantable medical device", U.S. Pat. No. 7,392,089 (Jun. 24, 2008)), but again these inventors fail to solve the problem of the number of electrodes and the possible number of wires to use.

Brain stimulation is known to have other effects besides motor in nature. For example, R. Hu (R. Hu, E. Eskandar, Z. Williams, "Role of deep brain stimulation in modulating memory formation and recall" Neurosurg Focus. 2009 July; 27 (1):E3), discuss the effects of it in memory formation. Hu's work is an indication of the possible side effects that may occur if the brain stimulation, intended to stimulate a certain part of it, goes beyond the intended area.

A good analysis of the pros and cons of the use of direct electrical brain stimulation can be found in B. Kluger et al., (B. M. Kluger, O. Klepitskaya, M. S. Okun, "Surgical treatment of movement disorders" *Neurol Clin.* 2009 August; 27(3): 633-77, v. Review.).

Finally, there is the problem of DBS in children, whose brains are guaranteed to change size, thereby invalidating the initial positioning of the implant. W. Marks (W. A. Marks, J.

Honeycutt, F. Acosta, and M. Reed "Deep brain stimulation for pediatric movement disorders" *Semin Pediatr Neurol.* 2009 June; 16(2): 90-8. Review.), review the use of DBS in children. This is a particular interesting and valuable application of our device because as children grow, the distal extremity of the implant slides away from its initially implanted location. With our device, with its larger number of electrodes, there exists a larger latitude of reprogramming to continue stimulating the same area (volume) of the brain after it slipped away due to growth.

Brain electrical stimulation is made with an electrode capable of delivering electric current to a chosen area (volume) of the brain. There exist two general classes of brain stimulators: cortical and deep brain stimulators. In a later section I will describe a preferred embodiment of my invention for deep brain stimulation, and accordingly I will describe here a current art used for deep brain stimulation. Cortical brain stimulators, spinal (nerve) stimulators, etc., function on substantially similar principles, as known to the people familiar with the art, the adaptations for which are obvious to the ones familiar with the art. Similar adaptations of the invention disclosed below are also, mutatis mutandis, used for measurement devices, that is, for electrodes designed to measure the electrical activity inside body cavities, particularly at the neurons. Similar adaptations of the invention disclosed herein are also possible for cardiac stimulators, for example. Cardiac stimulators can also improve with more precise location of the electrical stimulating pulses, as provided by our invention.

A DBS (Deep Brain Stimulator) is an electrical stimulator device composed of a battery for electrical power, an electronic circuitry for electrical pulse generation of appropriate amplitude, frequency, pulse width and shape, connecting wires and a wand, or lead, or picafina, from now on referred to as the picafina, that delivers an electrical pulse to the brain target location. Picafina is the supporting structure used by the main embodiment of our invention, generally similar to the devices used in Deep Brain Stimulation but potentially with far more tips or electrodes than DBS devices, which is strong enough to allow it to be inserted in the brain or other body structures, and which contains the necessary wires for connecting the measuring tips and the address decoders with the controlling and measuring instruments. For use in human animals, he dimension of a type I picafina is approximately the diameter of a wide drinking straw (5 mm.), its length being the necessary to reach the desired depth in the body. For smaller animals (as a mouse), the picafinas would be accordingly smaller, both in diameter and length, while for larger animals (as a whale or an elephant), the picafinas would be accordingly larger. The battery and microelectronic circuitry are housed in a hermetic sealed housing of material compatible with human tissue. This housing is typically implanted under the clavicle or somewhere else in the chest, from where extension wires are passed under the skin up the neck, usually behind the ear, to bring the electrical pulse from the generating box to the picafina. Alternatively the programmable oscillator and battery are located on the patient's skull, as disclosed by Pless et al., U.S. Pat. No. 6,810,285, or by Janzig et al. "Low Profile Implantable Medical Device" International Application No.: PCT/US2003/038927, but the physical location of the electronic circuit and battery are of no importance for the functioning of the device disclosed in this invention. For DBS, the picafina is inserted from a burr hole on the top of the skull, vertically down, deep within the brain, to deliver the electrical pulses at some appropriate target area. The picafina, which is the only part inside the brain, has the approximate dimension of a 3 in. long drinking straw: 7 cm long, 3 to 5 mm diameter. At the picafina's distal end there are typically four metallic rings, each one individually connected by an independent wire that runs inside said picafina to the proximal end of it, then, via extension wires to the electrical pulse generator usually implanted in the patient's chest. Each metallic ring is able to originate an electric pulse of a few volts, 90 microseconds pulsewidth, 180 Hz frequency (that is, 5.55 milliseconds between pulses), all typical values, varying from patient to patient, also varying with time on the same patient. The pulsewidth and frequency are usually the same for all patients, while the voltage depends on the patient, as well as which rings are connected. It is conjectured that the required variations in the applied electric potential (voltage) are consequence of changes in impedance perhaps caused by deposits on the ring-shaped electrodes, but the reasons for this do not impact our invention. Examples of current art picafinas can be seen at the Medtronic website.

Dennis D. Elsberry, Mark Rise and Gary King (Dennis D. Elsberry, Mark Rise and Gary King, "Method of treating movement disorders by brain stimulation and drug infusion" U.S. Pat. No. 6,094,598 (Jul. 25, 2000)) disclosed in 2000 a device that relies on both drug and electrical current delivery to affected areas of the brain, as a control to motion disorders, as our invention does. Their device lacks the flexibility of choice of electrical initiation point that our device has. Our device is only electrical, not chemical though, as are the majority of current DBS (Deep Brain Stimulation).

The multiplicity of contacts also serve to adjust the exact point at which the electrical current is injected into the brain, because it is known to be difficult for the neurosurgeon to position said picafina on a target area that the neurosurgeon cannot see inside the brain, with precision better than a few millimeters away from the desired location. Ultimate current injection location is adjusted by selecting one or other (or several) of said contacts. Ring selection, and voltage selection as well, are made after surgery, in what is known as programming sessions, during which information is send by telemetry (radio waves, magnetic links, or their equivalents), during which the device is adjusted for the particular needs of the patient.

Current art suffers from many problems, some of which are as follows. If the electrical contacts are circular rings, the current is injected 360° around the picafina, approximately the same amount in all directions, and reaching the same distance from the picafina on all directions. Therefore current art does not solve the problem of directionality, apparently because nobody has been able to have a large number of point-like smaller electrical contacts all over the picafina, and capable of being independently turned on or off as needed. This lack of directionality is not good because the picafina is seldom positioned at the dead center of the target location— the surgeon cannot see inside the brain as he/she inserts the picafina, and the regions look the same anyway, so even if the surgeon were able to see the region near the picafina when it is inserted, it would make little difference for its positioning. The surgeon can, and indeed does, apply current as he/she inserts the device, then ask the patient, who is awake during surgery, what he/she feels or thinks, which feelings and thoughts are influenced by the electrical input, from which the surgeon can determine where the picafina is at that moment. Successive observations, during surgery, of the effects of electric stimulation as the neurosurgeon inserts deeper the device allows him/her to eventually find the target location— but hardly the dead center of the target location. Indeed, though the relative position of all brain structures is substantially the same on all patients, their physical sizes, and therefore their absolute position with respect to any fiducial mark, say, the picafina's entrance hole on the skull, is not the same. This is true for internal as well as external features: all humans have their noses above their mouths but their absolute distances measured from, say, the forehead, vary from individual to individual. It follows that the electrode positioning is less accurate than desirable. Exact position of the picafina is also difficult because of the target regions are usually small, of the order of a few mm only. This imprecision in positioning causes then that either the current will not spread through the whole volume of interest, or else will spread outside it (see FIGS. 10a and 10b). Neither is satisfactory, because when the electrical current does not perfuse the target area there is under-treatment, while when the current invades nearby areas there may occur side effects due to stimulations of areas that are not intended to be stimulated. Neither is good for the patient. Both cases are known to exist, and because no solution has been found to control the injected electric current to different distances toward different directions, neurologists just accept them as fact-of-life. If the picafina is of a newer type, already in the market, with square or circular pads, the current can be injected in one or more directions, as needed, but with insufficient positional control, also not ideal for the patient. The inventors know of a Medtronic Inc. (710 Medtronic Parkway/Minneapolis, Minn. 55432-5604) picafina with 12 small pads of approximately 1 mm diameter, which is insufficient in number to precisely direct the injected current towards a preferred direction. It appears that Medtronic is trying to solve the directional problem but have been unable to add more pads, most likely due to lack of space for individual wires inside the picafina. Indeed, the very introduction of the few individual electrical contacts indicate that the need for many controllable points is known, though the solution has been eluding the practitioners of the art. Our invention solves this problem of controlling a large number of electrical pads, a known problem which solution have been eluding the practitioners of the art.

It stands to reason that in all cases when the inserting rod is close to the edge of the target region, shooting the current in all directions is not desirable, as the current will enter in areas that would be better left alone, as they are functioning normally. Indeed, DBS side effects are known to occur, which can be of a motor nature, as facial pulling, etc. but also of a mood or personality nature, including increased/decreased aggressiveness, depression/elation, etc. It is therefore desirable to have a means and a method to direct the electrical current into some specific direction only, starting from the imperfect positioning of the picafina, a problem that is not addressed by exiting DBS devices.

Analyzing the disclosed inventions and products in the market, it seems that the practitioners of the art are all aware of the desirability of having available the possibility of precisely controlling the point of insertion of the stimulating current in the brain (or heart, or spinal column, or etc.), for which only the obvious solution has been tried, which is to precisely position the stimulating electrode in the target region. Another possibility was never investigated, which is to implant a large number of small electrodes in the general vicinity of the target area, followed by the selection of the correct initiation point out of the large number of them. It seems that the last possible solution have not been tried because of the large number of wires necessary to connect each pad or contact to the electric power and electronics circuitry outside of the inserted electrode.

Other details on the current art picafina are known to the ones skilled in the art, while still others are unknown manufacturers' trade secret.

OBJECTS AND ADVANTAGES

Accordingly, several objects and advantages of my invention are

1. The possibility of controlling a large number of electrical pads for electrical current injection or measurements from a multiplicity of points, 2. The possibility of controlling which said pads are connected or not, at any given time, with capabilities of making such selection after the device is implanted in the patient, therefore selecting the measurement location with accuracy of the order of the separation between the pads, 3. The possibility of having many pads sharing the power wires and ground, 4. The possibility of having a small number of wires and a much larger number of electrical pads capable of initiating electrical stimulation, 5. The possibility of effectively using the small space available for connecting wires in the long and narrow picafina body, so as to have a much larger number of electrical initiating pads than wires running inside said picafina, 6. Releasing the picafina from having a dedicated wire running through the length of the picafina to each said pads, because there is not enough room in the body of the picafina for many wires, 7. The possibility of housing and running through the picafina's limited space a smaller number of controlling wires from O&A (Objects and Advantages) #1, when a larger number of wires would be impossible to fit.

8. The possibility of having some control on the direction and radial distance of the injected current in DBS with the adjustment of the size and shape of the compound electrical pad (the aggregate of many small pads), which occurs due to the effect known as "field shaping", 9. The decrease or elimination of electrical currents in adjacent parts to the target volume that are not intended to be electrically stimulated, therefore reducing known and/or unwanted side effects.

10. To conscribe the current injected in the brain by said picafina within a better defined angular distribution when compared with prior art, keeping it conscribed to the desirable area.

11. To conscribe the current injected in the brain by said picafina within a better defined radial distance from said picafina, when compared with prior art, keeping said current conscribed to the desirable area, 12. Approximately shaping the form of the volume around said picafina on which electric current is injected, to better conform to the target region 13. To further conscribe the injected current to a more precisely defined target volume in the vicinity of said picafina and conforming more with the target volume than prior art picafinas.

14. To offer a means and a method to direct the electrical current into some specific direction only, starting from the imperfect positioning of the picafina.

Other objects and advantages include increasing battery life as a consequence of the elimination of current flow in unwanted brain areas, which is a valuable improvement on a battery operated device which requires invasive surgery for battery replacement when said battery uses up all the stored energy.

Thus one of the problems that this invention solves is how to make a very large number of electrical pads on the surface of said picafina, in such a way that each of said pads can be individually connected to an electrical energy source. Further, besides making asymmetric electric fields and currents around the supporting picafina, preferentially directed toward one particular direction, this invention permits some shaping of the electric field in the vicinity of said picafina, which in turn keep the injected current in some desired brain locations, or particular shapes, around the picafina, further confining the current to the most desirable brain location. Such shaping of the electric field is known in physics and mathematics as field shaping, and is widely used, including in medicine. Nedzi (L. A. Nedzi, H. M. Kooy, Alexander E 3rd, G. K. Svensson, J. S. Loeffler, "Dynamic field shaping for stereotactic radiosurgery: a modeling study", Int J Radiat Oncol Biol Phys. April 2; 25(5):859-69. (1993)) describes one such use, in this case for radiation therapy. More details about field shaping can be found in Reitz (John Reitz, F. Milford and R. Christy "Foundations of Electromagnetic Theory", Addison Wesley (1980)) and Jackson (J. D. Jackson, "Classical Electrodynamics", Wiley, 2' ed (1975)). Summing up, one of the objectives of this invention is to provide a physical means and a method to confine the electric current injected in the brain to an arbitrarily shaped volume that can occupy a part only of the surrounding space around the penetrating rod that supports the electrode.

Indeed, on a picafina with hundreds or thousands of pads for electrical stimulation, it would be from difficult to impossible to dedicate a power wire to each point-like electrode on said picafina, the difficulty increasing with larger number of electrodes. The electrodes in the stimulator of our invention are instead all connected to the same power carrying wire, or to a few of them, through a dedicated digital switch that can be turned on and off with a digital addressing system. Moreover, since the objective is to keep a plurality of point-like electrodes active at the same time, instead of being active only while addressed, the address switch also contains a delay line which keeps the power switch closed (on) for some time after having been addressed. Given the stimulation pulse length, which is of the order of 100 μs, and the time needed to assert each address line, which is of the order of a few ns, or 10,000 times shorter, the total time elapsed from addressing a first point-like electrode to a total of a few hundreds electrodes (at a few ns each) is still less than 1 μs. Thus, the delay between the individual point-like electrodes is negligible with respect to the total pulse width, which in turn means that the biological effect occurs as if the electrodes were simultaneously turned on/off. Note also that all electrical neuron signals occur over times of ms, which is one million times longer than the delay in assertion between one electrode and the next.

For the benefit of the readers not familiar with electronics, we introduce now a common concept in electronics. Latch is a term used in electronics meaning the capability to keep some particular configuration, or output, or logic, or selection, even after the selecting source, etc., is no longer active, or even if the selecting source is changed to a different value. Another way to look at it is that a latched device has memory to keep a configuration when instructed to do so. A standard wall light switch is an example of a latch because it keeps the last state it was set by a human being, either on or off. Another similar way to achieve the same objective is to use a latch to keep the electrode tip indefinitely connected to the power source, in which case the pulse shape is created by the electronics that controls the battery output, as in current devices.

Further objects and advantages of my invention will become apparent from a consideration of the drawings and ensuing description.

SUMMARY OF THE INVENTION

The invention is a method and a means to provide a large number of electrical pads from which electrical current can be injected in live animal tissues, as in artificial muscles, heart pacemakers and defibrillators, and specially in neural tissues in general, as spine and brain, as well as other similar applications. The invention can also be used on the other direction, to make electrical measurements of the electrical activity of animal cells, measurements that can add in the determination of the placement and level of electrical stimulation. The need for a large number of pads, or points from where to inject the electrical current, exists because it is impossible to position the device with any accuracy, so that final place adjustment is made by trial and error trying one (or a group) of pads until the best one(s) is (are) discovered.

The need for such a large number of pads has been recognized for a long time, but never a solution was found on how to accommodate the large number of wires in the small space available, one wire for each pad, even if a common ground is used. Our invention solves this problem using a single power wire common to all pads, that is in turn connected to as many pads as necessary with a digital addressing system that turns on or select any desired pad with a smaller number of address lines (wires).

This second problem is solved by our invention with a delay line, which causes that any pad that is turned on stays on for a selected time after the address line is changed to select another pad. We now define "bus", which is a common term in use in digital electronics. In digital electronics a bus is a set of wires grouped according to its function. For example, the address bus is the set of wires which carries the address value for something, the data bus is the set of wires which carries the data, or numerical value for something. The pulsewidth (time on) is necessarily on the order of milliseconds (typically 0.1 to few ms), compatible with biological times, while the address assertion (time to assert a new address on the bus) is of the order of few nanoseconds (frequency of order 100 s MHz), typical of modern electronics. It follows that the address change is so fast when compared with the other times involved as to be instantaneous from the point of view of the biological events and pulsewidth. This combination of virtually instantaneous address line selection of pads with a much longer (known as "infinite" in science and engineering) power on time, creates the desired result of a multiplicity of pads (virtually) on at the same time for the desired duration.

BRIEF DESCRIPTION OF THE DRAWINGS

FIGS. 4a, 4b, show another version of the picafina of our invention with a larger number of smaller electrodes.

FIGS. 7a and 7b show the location of the address decoders and electric switches associated with each electrode pad.

FIGS. 8a and 8b show one of the possible implementations of the electronics used for the alternative embodiment of our invention using several measuring pads and several signal carrying wires.

FIG. 12 shows a redundant wiring at the proximal end of the picafina of my invention. Each wire is repeated for redundancy, to be used in case of wire breaking, which is common given the small size of the wire.

DETAILED DESCRIPTION

Main Embodiment

Figure 1:
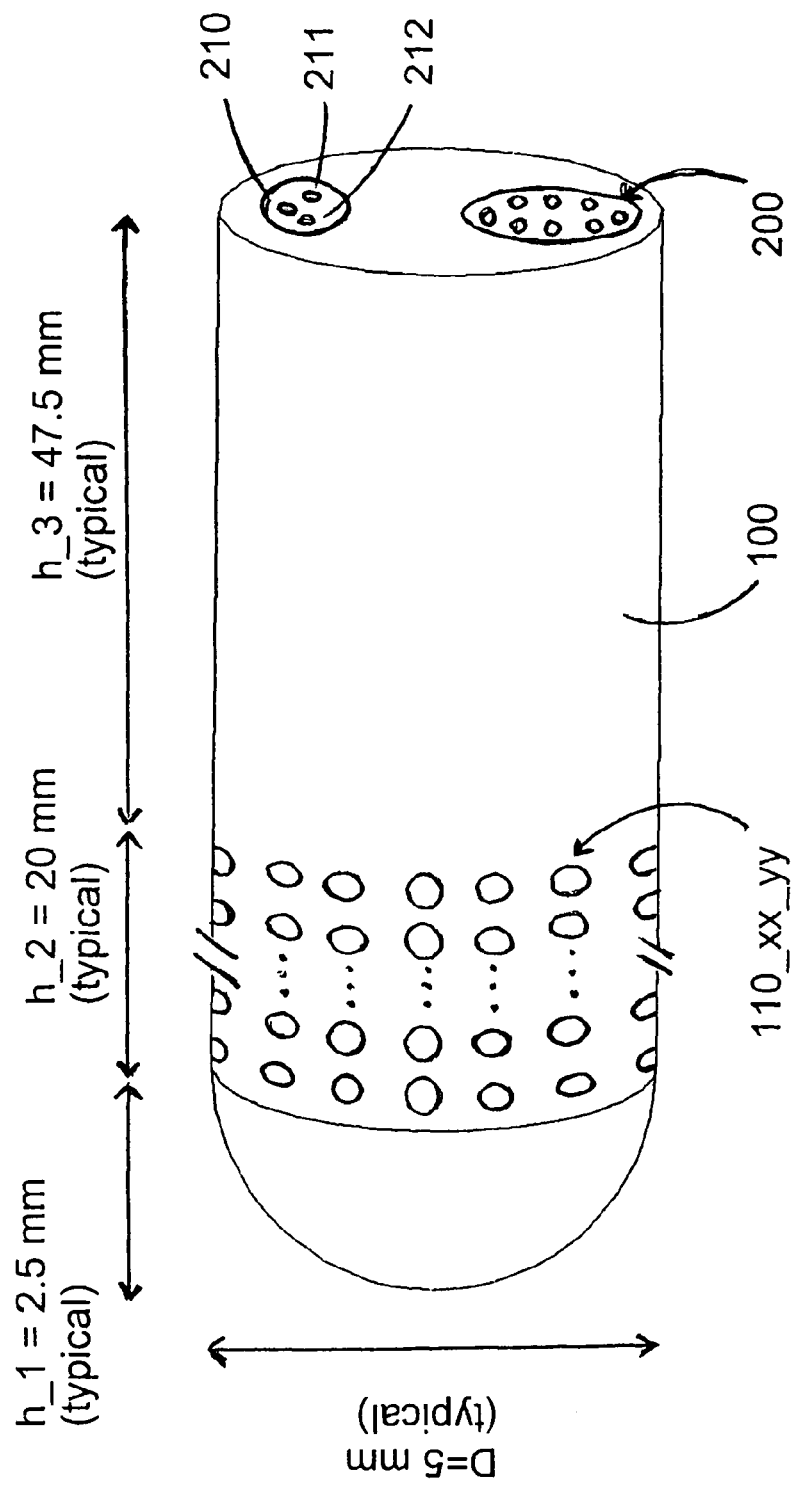
FIG. 1 shows the picafina of our invention with a possible configuration of circular shaped electrodes.

For the disclosure of my invention I will use the example of deep brain stimulation (DBS), it being understood that the same method applies to other stimulators, with the modifications that are obvious to ones familiar with the art. A similar method also applies to measuring electrodes, that is, devices to measure the electrical signals in living organisms. A similar method also applies to bi-directional devices, which are capable of both reading electrical activity in the neurons and also capable of stimulating other neurons, or the same neurons after the measurements were made, which are very useful for electrical stimulation because the current state of the neurons can give indications of the location, type and level of electrical pulses to be applied.

I start with a succinct description suitable for electrical engineers, then follow with a detailed description for readers with non-electronic backgrounds. The problem is to deliver electric current to internal body parts, as brain, spinal cord, heart or muscles, which may even be not visually accessible, or that for some any other reason cannot be precisely located. A source, here called picafina, larger than the point of delivery of current, is then approximately placed in the target location, such source covered with a multitude of surface electrodes, here called electrode tips, or just tips, or pads, which are of such a size and placement as to cover all the desired target areas and more. After a surgeon implants such source in the general vicinity of the target area, a medically trained person can select which pads to use, typically by observing the desired effect from turning on one pad at a time, or a combination of pads at a time. It is relatively easy to make a very large number of small pads to precisely control the place from which to inject current, but it turns out that there is a stringent limit on the number of wires which are needed to connect these pads to the battery and controlling electronic circuit, because these wires have to go through the limited space available in the body into which the picafina must be inserted. So current technology stimulators, in animals, including human beings, the limited space available limits the number of pads to the number of wires possible to use—each pad needs a wire connecting it to the power source. Current technology can put a few dozen wires at maximum in the limited available space, therefore a few dozen pads only can be used (Gregoire Courtine, private communication). To make use of more pads than wires, this invention discloses the use of a digital addressing system coupled with a timed delay system, and a latch, which, under the control of a microcontroller or equivalent device, turns on a subset of a large number of pads capable of delivering electric current to the body. The subset is chosen with the objective of delivering the current to selected parts of the body, the parts that are in the neighborhood of the selected pads. The timed delay keeps the current on for a pre-determined time after selection of each pad, because typically it is desired to have many pads on at the same time, so any selected pad have to stay on after another pad, or many pads, is (are) being selected. The timed delay is much longer than the time taken to select each pad (time for new selection<<time pad on), such that out of a negligible small initial time delay (order of nanoseconds) all pads are on together (order of 100 microseconds). Alternatively, once a pad(s) is (are) selected, they stay on indefinitely, in which case the electronic controlling associated with the battery turns the current on and off according to the desired pattern, in which case all the pads are on together and off together. This latter possibility is more similar to current art. It lacks the provision to add a delay between the pads, which is offered by the time delay, which offers more options for treatment.

The invention can also be used on the other direction, selecting one out of a plurality of pads from which to read electric potentials, in this case to obtain information about the body, instead of to act on it. It will be apparent to the ones skilled in the art that readings the actual neuronal firing can give information to the type of stimulation required to achieve the objective, which in this main embodiment of DBS is to stop Parkinson disease tremor.

DETAILED DESCRIPTION

Figure 10:
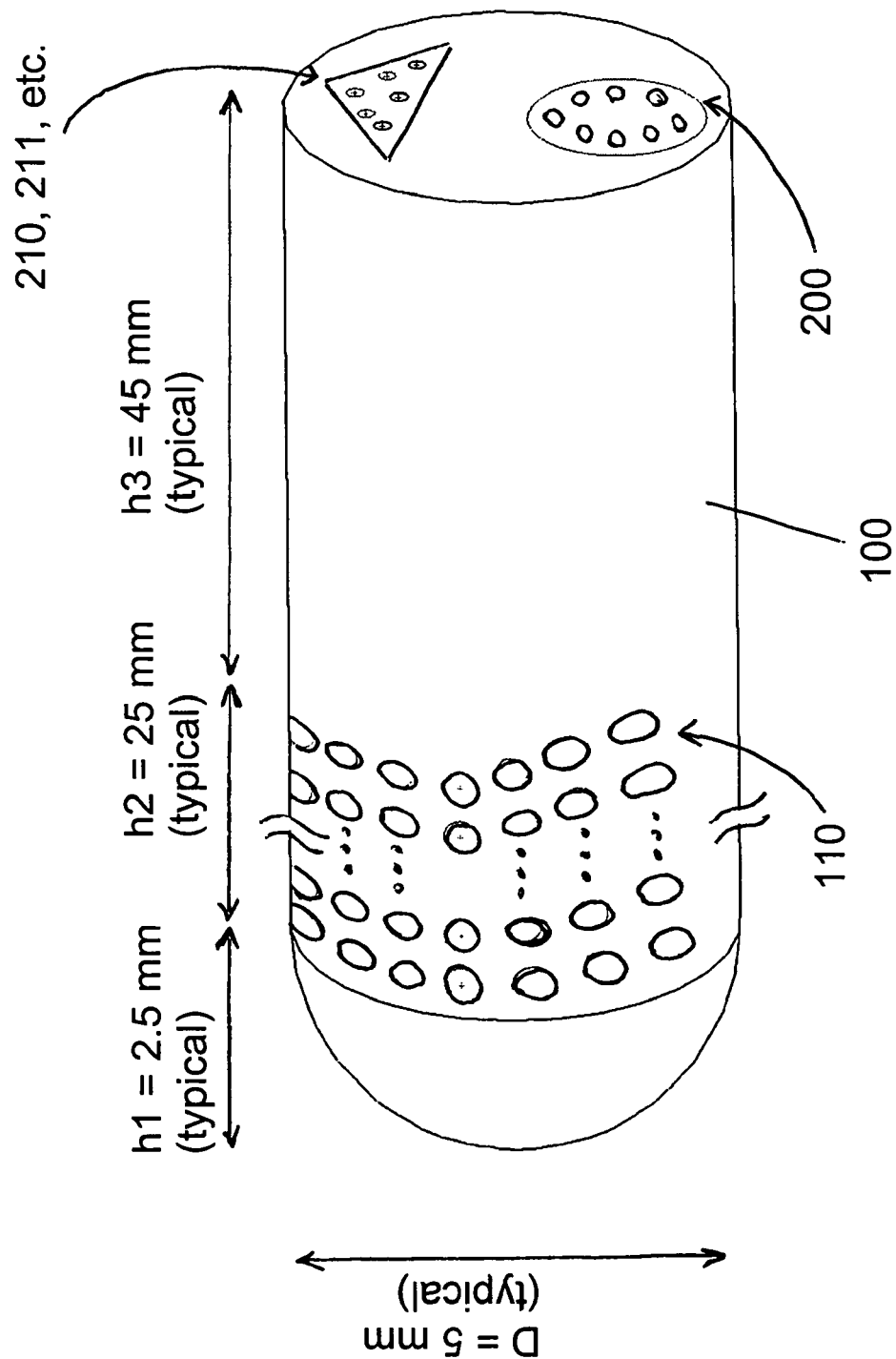
FIG. 10 shows a main embodiment of my invention with 12 electric pads around the circumference of the picafina, 16 ring of pads along the z-dimension, and no electric pad on the tip of the picafina.

FIG. 10 shows a perspective view of a basic version of our invention for a particular main embodiment used for deep brain stimulation. For brain stimulation, the objective is to inject electrical currents in selected areas of the brain, the objective being to modify some brain activity, often motor in nature, as in Parkinson disease, or epilepsy, but other characteristics are also modifiable, including mood and personality. It displays a possible main embodiment of my invention omitting the inner electrical connections and structures, which are described immediately after. The picafina's outer surface is made of some material compatible with human tissues, e.g., polyurethane (for the bulk) and gold or titanium (for the metallic pads), these being only examples used in current art picafinas, many other materials being possible, and the particular material being irrelevant for our invention. The body has to be of a material that does not conduct electricity, while the pads are made of a material that is a good electrical conductor, as a metal. The pads are to serve as starting points of electrical currents somewhere in the body, which, for the main embodiment, is deep inside the brain. The same principle works in reverse, to read one out of a plurality of electrodes to obtain information, but the reading device is different in some characteristics.

Starting from the distal tip of the device, FIG. 10, near the concave end of the picafina of our invention, and following only the external features of it, there is a solid, smooth part of length $h\_1=2.5$ mm (typical value), after which the electrical pads start, on a length $h\_2=20$ mm, followed by another smooth part on a length $h\_3=47.5$ mm, for a total length h_total=70 mm (typical values, see FIG. 10). The distal end is shaped as indicated in FIG. 10 to facilitate the insertion of the picafina into the mushy brain tissue, while the proximal end (near the skull) is flat, to facilitate the electrical connections and mechanical sealing. The proximal extremity is usually flush with the skull, to which it is affixed with screws or their equivalents (not shown). At the picafina's proximal end there are a number of wire endings with the necessary means for connection to extension wires that make connections to the outside of the skull. In this main embodiment there is only one power wire (voltage), one ground wire, and a plurality of address wires (8 in this main embodiment). It is also possible to have a deselect line, or wire, the function of which is to disconnect all switches and gates, or turn them all off.

The dimensions indicated in FIG. 10 are typical, for concreteness of the description herein, different values to adapt to different situations being possible, as known by the practitioners of the art, and these dimensions should not be therefore considered restrictive to the invention, but only typical and compatible with the particular application detailed here: Deep Brain Stimulation (DBS). Moreover, the number of pads is here artificially set to a low value to make the drawings and the description easier to follow, a real case picafina having many times more electrical pads than the illustrative example used here. In this main embodiment described here there are only 192 pads, numbered not sequentially but accordingly to the rings they belong as 110_01_01, 110_01_02, 110_01_03 etc, until 110_01_12, for the 12 most distal pads (i.e., on the most distal ring of pads), then 110_02_01, etc. for the next ring, etc. until the most proximal ring of pads, which is numbered 110_16_01, etc., in FIG. 10. These pads are made of metal, titanium in the maim embodiment, but any other material that is compatible with human tissue and also relatively good conductors of electricity is suitable. These pads are to be the initiation points to electrical currents to be injected inside a patient's brain. With the indicated dimensions, typical pad diameter is 0.666 millimeters and edge-to-edge separation is also 0.667 millimeters along the circumference, so center-to-center separation between the pads is 1.333 millimeters along any circumference at a fixed distance from any of the ends (fixed z dimension). On a 5 mm. diameter picafina, there are 12 such pads on a circle, at any particular distance from any of the ends. Along the z coordinate the separation between pads is also 1.333 mm (typical dimension), making 16 such circles populated with 12 pads each, making a total of 192 pads on a z dimension length equal to 20 mm ($h\_2$). These are possible dimensions, in no way to be taken as restricting my invention, as many other values being compatible with my invention, as known to the ones skilled in the art. The length h_total must be such as to reach the particular target area, and the diameter must be compatible with the size of the animal in which it is used.

Continuing towards the proximal end of the picafina of my invention, beyond the region marked $h\_2$ populated with electrical pads, the body 100 is bare, no pads, corresponding to areas on which electrical stimulation is not expected or needed. Typical dimension is $h\_3$=47.5 mm, for a total length h_total=70 mm=7 cm, which is a typical value for DBS.

At the proximal end of the picafina there is a plurality of wires which may have special connectors to make the electrical connection to extension wires to the electronic circuits and battery or any other power source, which are described further down in this section. Said connectors could be separated as one harness with 8 contacts for the address lines 200 and a separate harness for the power wires 210, 211, ground wire, and other wires as necessary, as shown in perspective at FIG. 10, or all the wires could end on a single harness, or each wire could have its own dedicated connector, or any combination of these, because the particular form of connecting the wires is not part of this invention. The technology for the connectors is an established art, my invention making no improvement on this aspect of the picafina. Moreover, the technology used for the wire connections used in current art deep brain stimulators is suitable for my invention. For purposes of description we are here dividing these wires in address lines and power lines, concepts that are explained below but are standard concepts in electrical engineering.

Figure 2:
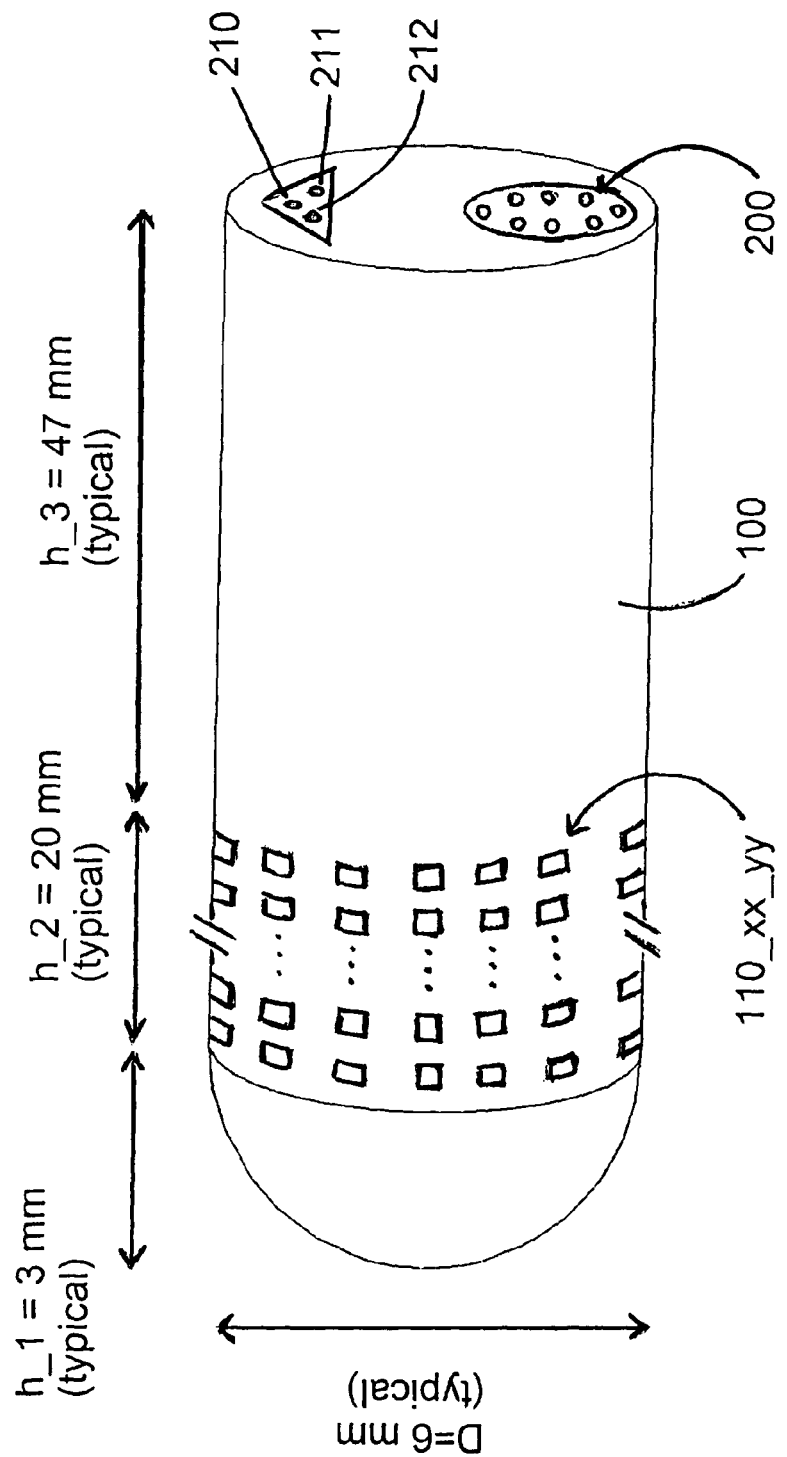
FIG. 2 shows the picafina of our invention also with electrodes equally space as in FIG. 1 but with electrodes of a square shape.
Figure 3:
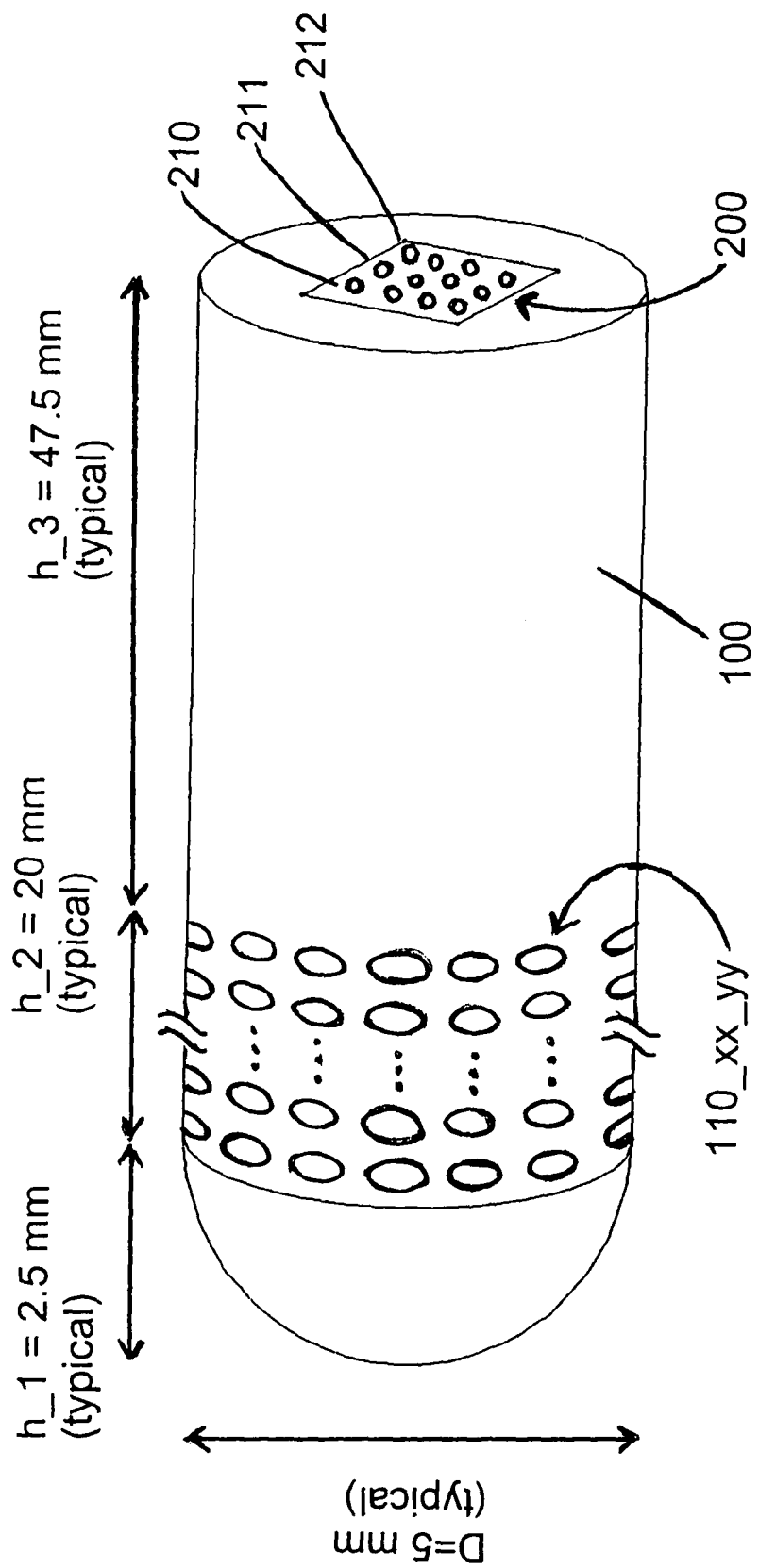
FIG. 3 shows the picafina of our invention also with electrodes equally spaced as in FIG. 1 but with elongated electrodes along the circumference direction.
Figure 4A:
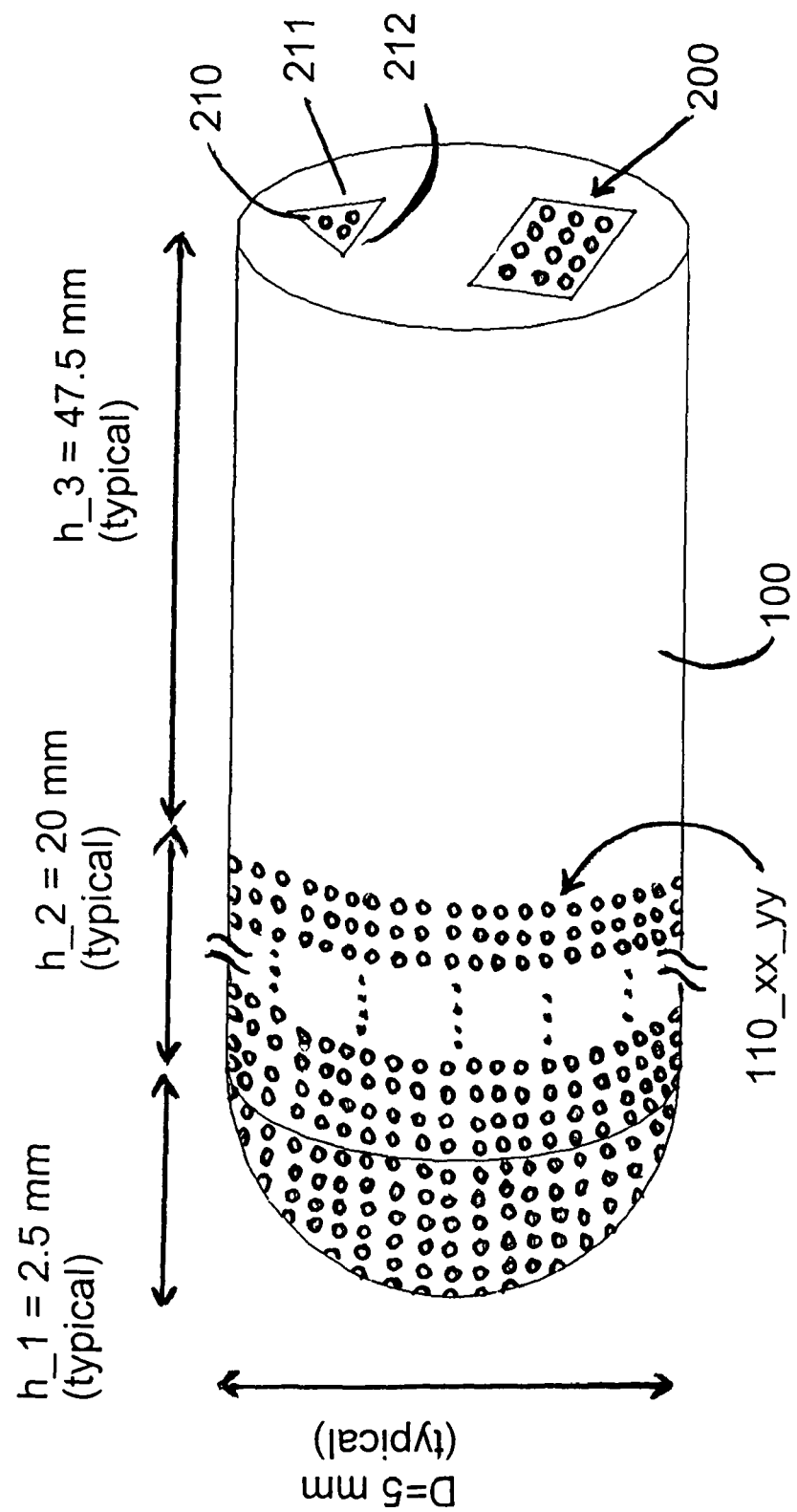

FIGS. 4*a*, 4*b*, show another version of the picafina of our invention with a larger number of smaller electrodes for a larger electrode density as compared with FIGS. 1 through 3. FIGS. 4*a* and 4*b*, depict a side view and proximal end of this version. FIG. 4*b* depicts a flat view of a possible proximal end of the picafina 100 of our invention. The positioning of the wires is not part of our invention, the particular location displayed at FIGS. 10 and 4*b* being exemplary only.

Describing now the inner structure of the picafina 100, also starting from the distal end of it, or lower part of FIG. 10, the first 2.5 mm of it ($h\_1$, typical dimensions) have no features inside. In the particular preferred embodiment, said distal end is solid and made of the same compatible material as the external surface of the picafina, but this is not necessary, it being possible to have a hollow interior, or an interior made of a different material then the exterior surface, this detail not being part of the invention herein disclosed. It is only necessary that picafina 100 has sufficient stiffness and durability. Moving towards the proximal end of the picafina, on its outer surface, at the distance $h\_1$ from said distal end (see FIG. 10), there is a first set of electrical contacts or pads, 110_01_xx (xx running from 01 to 12), along an imaginary ring on its outer surface, at a fixed z-coordinate. With the typical, exemplifying dimensions given above, 1.33 millimeters center-to-center distance between electrical pads, picafina radius R=2.5 mm, there are 12 such pads around the picafina's outer surface making the first ring of pads. These electrical pads are connected to electrical circuits inside de picafina, as we proceed to describe.

FIGS. 7*a* and 7*b* show the location of the address decoders and electric switches associated with each electrode pad and one of them with the most important (not all) connections indicated. Note that FIG. 7*a* is an example of each one of the multiple address decoders and switches, one at each z-value, that is one at each cross section at a fixed distance from one of the two extremities of the picafina of our invention. FIG. 7*a* is a conceptual drawings of a cross section of the picafina of our invention, made perpendicular to the long, or vertical, or z dimension shown in FIG. 10, made at a distance approximately 2.5 millimeters from the distal end, that is, at the plane of the lowest (closest to the distal end) ring of electrical pads. What is shown in FIG. 7*a* is not a drawing of what would be seen in reality, with a microscope, but a representation of the electronics at that position, the actual transistor construction being out of the scope of the invention, not included in the invention, and part of the old art of semiconductor and printed circuit board manufacture. While FIG. 7*a* depicts a schematic (simplified) view of the electronics circuits that determine our invention, FIG. 7*b* shows in more detail the electronics for one single electrical pad, one of the 12 repeated circuits around the circle at FIG. 7*a*. The reader is requested to pay particular attention to these figures that detail the electronics of the picafina of my invention. Referring to FIG. 7*b*, when address for pad 110_01_01 is asserted on the address bus 200, that is, when 200 has value (0000 0001) the address decoder 830_01_01 recognizes the address and makes its output to go high, while none of the other address decoders recognizes the address as theirs, so all other address decoders keep their outputs low. This in turn causes the output of timer or pulse stretcher 820_01_01 to go high (but none of the other timers) and to stay in that high state for a predetermined length of time, which for the main embodiment is 90 microseconds. As long as the output of the timer/delay 820_01_01 is in the high state, which turns switch 810_01_01 to the conducting state thereby connecting the measuring pad 110_01_01 to the power wire that runs along the length of the picafina, all the way to its proximal extremity, where the necessary connections are made, in this case, the connection of the power wire to an appropriate source of electrical power, at some pre-assigned voltage, for example. It is common among electrophysiologists to call a measuring pad or a measuring tip the very tip of the measuring wire, sometimes referred as electrode in current art, made of metal or some other electrically conducting material. In current art devices the measuring tip is generally at the end of a thin, stiff wire, typically 100 micrometers diameter, separated by 100 micrometers, or more, while in our invention the measuring tip is a metallic area as small as a few micrometers, typically 5 micrometers but can be less or more according to the need, separated by as little as 5 micrometers, at the surface of the device of our invention. Current art is capable of manufacturing measuring tips for our invention that are less than one micrometer in diameter, and the shape is not necessarily circular. Alternatively, a measuring pad can be referred to as a neural sensor. As used here, the term "neural sensor" means an implantable device for sensing neural signals. Examples of neural sensors include microwire electrode arrays, optical sensors, microwires, magnetic field detectors, chemical sensors, and other suitable neural sensors which are known to those of skill in the art upon consideration of the present disclosure. Switch 810_01_01 could be, for example, an NPN transistor (not shown) with the necessary biasing, so whenever there is current at the base of transistor 810_01_01, which is controlled by resistor 805_01_01 (not shown), said transistor is on the low impedance state (conducting state), whereby pad 110_01_01 is connected to the power wire. While transistor 810_01_01 is on, the electrical pad 110_01_01 sees a low impedance connection to V_cc, or, in other words, it is connected to the power supply at V_cc minus the (small) voltage drop at transistor 810_01_01. It follows that, as a consequence of this sequence of events, current flows out of electrical pad 110_01_01 into the patient's brain, causing the desired effect on its function for the duration of the pulse from timer/delay 820_01_01, which is 90 microseconds for this main embodiment, or the standard time currently adopted for the pulses out of the rings in current art picafinas. None of the other pads is turned on at this stage.

FIG. 7b shows the electrical connections between the main conceptual blocks of my invention: the address decoder, the timer/delay and the electronic switch, and the wiring for them, the address bus and the power wire.

A few nanoseconds after the above event is completed, and as fast as microcontroller 1200 (not shown) can implement new events, it asserts a new address on address bus 200, say 0000-0010_B=02_D=02_H (from now on B/H/D after a number, or in subindex, stands for binary/hexadecimal (hex)/decimal number representation. For example: 1010B=0AH=10D), which is the next address, recognized by address decoder 830_01_02 as its own, and then, mutatis mutandis, the same process described in the above paragraph repeats for pad 110_01_02, which will then stay on concomitantly with pad 120_01_01 next to it, because previously selected pads continue on for 90 microseconds, a very long time for electronic events.

As microcontroller asserts all addresses residing in its memory, which corresponds to the pads programmed to inject current in the patient's brain, all pre-programmed pads are turned on, this occurring with a time delay between each selection much smaller than the 90 microseconds that the pulse lasts for this particular embodiment, resulting in that for all practical purposes the pads are on together. After 90 microseconds the timer/delay reach the end and begin turning each pad off in quick succession, which ends one cycle. Another cycle repeating all these steps is started after a time equal to 5.55 milliseconds for this main embodiment, or at a frequency f=180 Hz, the full sequence repeating indefinitely for this main embodiment, though it is conceivable that in some circumstances the sequence could be interrupted during sleeping or other times of the day.

Figure 9A:
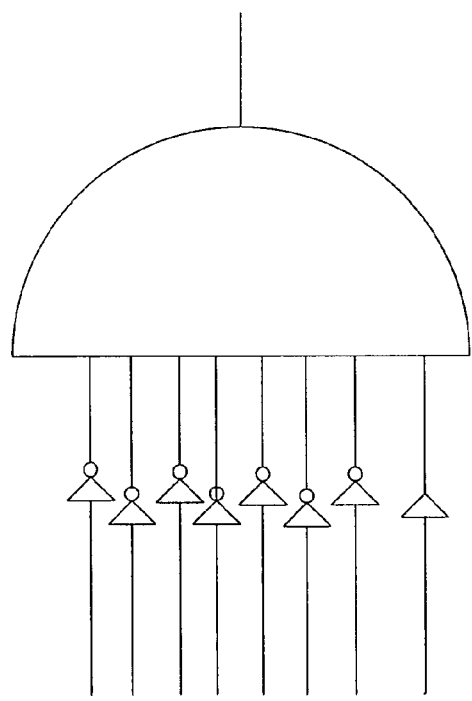
FIGS. 9a and 9b are possible implementations of an address decoders.
Figure 9B:
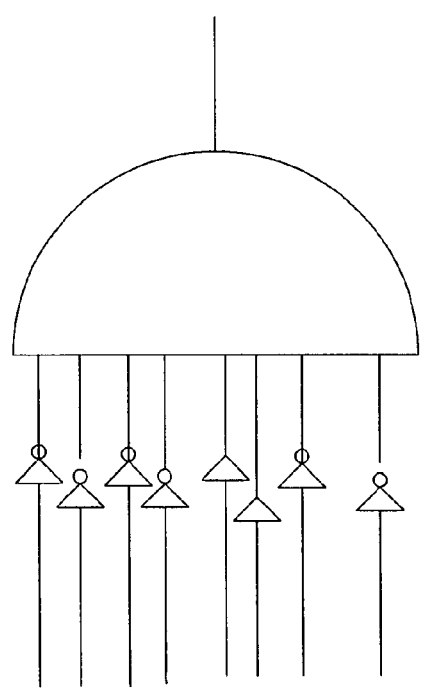

FIGS. 9a and 9b show two possible implementations of address decoder 830. Our invention is not limited to this particular form of address decoder, which is here shown only as an example. Indeed, our invention does not improve on the art of address decoding, which is a mature art in electronics and is just used here. The inputs to each AND gate are preceded or not by inverters, as needed to make the address for a particular electric pad. FIG. 9a decodes for address 01_D=0001_B=01_H, or the first pad on the first, or most distal "ring" of pads, while FIG. 9b decodes for address 12_D=1100_B=0C_H (8+4), which is the last pad on the same most distal "ring" of pads. As seen, with an appropriate combination of inverters any desirable address can be selected by address decoder 830. This is only an exemplary version, many other possibilities existing for address decoders, which is a mature field in digital electronics, not part of my invention and any of the variants being possible for my invention. In the preferred embodiment of my invention said address decoder is also grown on the substrate of each layer that serves a particular set of pads 110 at a fixed distance from the ends of the picafina, for example, the 12 pads described above, part of the most distal "ring" of pads. As is the case for the switch and pulse stretcher, the address decoder should be build in such a way as to minimize power consumption.

Returning to FIG. 7a it shows the electronic circuits existing at that cross section, not necessarily at their exact position, as the positioning of the electronic parts is not part of my invention, but only their function and logical connection. The detailed implementation of the electrical connections are known in the art of electronics. In particular the actual transistors and electrical connecting wires most likely will in practice be not on a single plane but on different layers, according to the established art of transistor and printed circuit board manufacture. Both transistor and printed circuit boards are mature fields on which my invention makes no improvements. Our invention works with this electronics that are described in this layer or some of its electronics equivalents.

For the main embodiment described, which has 16 "rings" of pads, each at a different z-coordinate, there are 16 circuits similar to the circuit described above, except for the addresses, which is unique for each pad.

Between each plane of electronics that feed power to each of the 16 "rings" of pads, there are vertical "wires", which are in this case are made using the established techniques of semiconductor manufacture or of printed board manufacture, or a combination of these, such "wires" connecting all the 8 address lines 200, the single "wire" 211 that carries the electrical power to the pads, the wire 210 that carries the power to the picafina electronics, the ground wire, and other wires that may be needed. Such vertical wires connecting in parallel all 16 planar circuits described above continue to the proximal end of the picafina, where they end at the connectors 200, 210 and 211 shown at FIGS. 10 and 4b.

Said wires running inside the picafina of my invention are, in the preferred embodiment here described, constructed with some combination of semiconductor manufacture, printed circuit technology and manual soldering. For example, all the address decoderes 830 and the switches 810 that serve a particular set of pads at a fixed axial distance from the ends of the picafina (say pads 120_01_01 through 120_01_12) could be made of current technology of semiconductor manufacture, and their connection to each of the pads could be individually made by a technician at fabrication, while the vertical connections from layer to layer could be made with the existing technology of vias, a known method in printed circuit technology. But printed circuit technology, or semiconductor manufacture, or manual soldering are not intended to be restrictive for my invention, any other equivalent technology or any combination of them being acceptable.

The switch 810 can be as simple as an npn transistor, as indicated in the schematic diagrams of the figures disclosing the main embodiment, or it can be a more sophisticated circuit, as known to the practitioners of the art of electronics, and the time delay/pulse stretcher can be any of the available circuits used by electronics engineers or it can be a new, especially designed circuit, the particular design of the pulse stretcher not changing the invention but just that such a circuit exists together with the on/off switch. One example of a pulse stretcher can be the very much used 555, manufactured by many chip manufacturers, set for a one-shot mode and with the appropriate pulse width set by resistors and capacitors as per manufacturer instructions. In the preferred embodiment of my invention the address decoder, the pulse stretcher and the switch 810 are grown on the substrate of each layer that serves a particular set of electrode pads 110 at a fixed distance from the ends of said picafina, for example, the 12 contact pads described above. For the switch, the pulse stretcher and all other electronics described in my invention, it is preferable that they use as few components as possible to conserve energy supplied by a battery.

From the connectors shown at the proximal end of the picafina at FIGS. 10 and 4*b*, wires of the necessary length (not shown) connect the proximal end of the picafina to the electrical battery and electronics circuit, including microcontroller 1200 (see FIG. 12 for a redundant version of the wire harness). Said battery and electronics are usually inside a sealed box (not shown) implanted in the torso of the patient, with the wires generally running under the scalpel, behind the ear, down the neck to the torso, but the particular places for the wires are not part of this invention. The position of the battery and electronics are not part of this invention; most current art battery and electronics are implanted in the patient's torso but some are also implanted in a cavity drilled on the skull, near the picafina.

A sealed box containing the battery and the electronics is connected to the address bus 200, power wires 210 and 211, ground wire and any other wire, as needed. Said power wire 211 is connected to a programmable device, controlled by microcontroller 1200 or microprocessor, or microcontroller, or DSP, either commercially available or especially designed, or any of its equivalents, which sets the output voltage to any of the possible values compatible with the battery and the electronics. Said programmable device, under control of the instructions sent to the microcontroller 1200 by the telecommunication link (described in the sequel), adjusts the voltage to some desirable value, determined by trial and error by the medical practitioner as he/she observes the effect on the patient that occur as he/she adjusts the voltage to several values, preferably following either his/her experience, or following some method indicated by the equipment manufacturer, as described in the sequel.

During normal operation, that is, after the adjusting phase described in the sequel, microcontroller 1200 has stored in memory, as downloaded by a telecommunication link described elsewhere, a list of numbers which are the addresses of the pads to turn on, which, under the control of a pre-stored program, is put on the address bus 200 one at a time, in quick succession, to turn on the pads as required. Said list of address can be as few as one single address of a single pad, or a large number of addresses.

The electronic circuit that controls the stimulator is comprised of an analog part and a digital part. The analog part of the electronic circuit adjusts the electrical energy source's output (e.g., a battery, a capacitor, or the like) for either a constant electric potential (that is, a constant voltage) or a constant current to be delivered to the pads at the picafina. The electric energy source output is connected to the power wires 210 and 211 that goes to said picafina, and to the ground wire as well, connecting to the power wires at said picafina's proximal end, which is generally at the burr hole aperture on the patient's skull. The electronics adjusts the electric energy delivered to the picafina for a constant voltage, typical values are 3 to 5 V, or it adjusts the electric current, typical values are 3 to 5 mA instantaneous current, but these are just exemplary values most commonly used in current art but that may deviate as the particular needs of each patient dictates, and the device should be designed to work on a range several times the typical value. There ought to have some system to adjust the voltage/current output for a particular value, which depends on the particular patient and may need to be changed as time goes on for the same patient, and one exemplary such system is described below. Such electric potential (voltage) or current changes are generally implemented without direct contact, e.g., via radio pulses, magnetic induction or some other convenient method, which is not part of this invention, as it is part of the current art. This part is not described in this invention because it is the current art of electric stimulators, brain stimulators, nerve stimulators, etc., so it is not part of my invention, and they can be any of the existing circuits known to the practitioners of the art.

The digital part of the electronics is a device based on what is generally known as Digital Programmable Device (DPD), as a microprocessor, a microcontroller, a Digital Signal Processor (DSP), or the like, including a memory part and ADC (Analog-to-Digital Converter) and/or DAC (Digital-to-Analog Converter). A microcontroller better describes the DPD, but it can also be divided in a combination of a microprocessor and a memory part and an ADC/DAC. It contains a digital memory part in which a program can be stored, as well as numerical parameters and even results from readings of the patient's condition at pre-assigned times or when a pre-assigned condition occurs. The stored program contains, among other things, the instructions to periodically turn on and off each of the electric contacts 110 described above. As is well known in the art, all DPD work with an oscillator, known as a clock or system clock, as shown by the standard PC, that powers up with the correct current date/time-of-the-day, usually on the screen's lower right hand side. The system clock is able to keep track of real time.

Said DPD is capable of creating the addresses of each of the pads selected by the medical practitioner, one at a time, in rapid succession, until all desired pads have been selected—usually not all of them. The pads are selected according to the programmed sequence determined by the medical practitioner. Said selection is made either using neurological knowledge, or prior experience, or just trial and error, or any combination of these methods. Typical times for each address to be asserted on said address bus is of the order of nanoseconds or tens of nanoseconds. The whole series of pads may be selected, one at a time, on a total time or the order of a fraction of to a few microseconds. After the series is completed, said DPD stays quiet for a longer period, which in current art is of the order of 5 milliseconds (frequency f of the order 180 Hz), after which time the whole sequence is repeated, said DPD again asserting all the addresses in rapid succession, etc.

Said printed circuit wires are built inside said picafina, layer by layer, horizontally, toward said electronic components and electrical contacts on said picafina surface, all around said picafina surface, and vertically, within the height of any given contact set to the next, from one level of contacts to the next, from the distal end of the picafina until all the contacts are printed on the outside surface of said picafina. The technology to grow (that is, to construct, or to build) the electronics inside said picafina is not part of the invention, and any of the existing art technologies can be used. For example, all the electronics for each "ring" can be grown on a thin substrate, which is later soldered by hand by a technician, under microscope, or by an robot-like soldering machine to said surface electrical pads and to said vertically connecting wires. At such distance along the picafina such that all the surface contacts are complete, a number of standard ending pads known to people experienced in the art of printed circuits can be printed, which can be connected to standard wires that are in turn brought to the proximal end of said picafina, or the whole picafina can be completely constructed by layer by layer deposition until its proximal end.

OPERATION OF INVENTION

In this section we will describe the two steps needed for the operation of the invention: the calibration and the use. Similarly as for the description of the invention we start with a disclosure of the operation written in a succinct form for electrical engineers, followed by a detailed explanation of the operation.

OPERATION OF OUR INVENTION

Electrical Engineering Version

Our invention discloses a system to have a very large number of pads from where to inject electrical current in the body, while using a much smaller number of wires to bring the electrical power to these pads. The invention operates under control of a microcontroller or similar device that has stored in memory a list with the digital addresses of the pads that are to be turned on. The pads' 90 microseconds pulsewidth, as well as the pulse repetition rate or 5.56 ms (frequency f=180 Hz) are standard in current art and fixed in the main embodiment. These are the values used by existing devices, which were discovered by trial and error, but these particular values are not intended as limitations to our invention, which operates with any pulse sequence. The microcontroller simply turns on in quick succession all pads that have been programmed to be active, then waits the necessary 5.56 ms to start a new cycle. The pads are automatically turned off after the required 90 microseconds by the timer-delay associated with each, while they are turned on by the microcontroller which is usually located on the patient's chest.

From another point of view, the operation of the invention is based on each pad being connected to the power wire via an electronic switch 810 that is turned on by a timer/delay circuit, which is turned on by a specific address decoder associated with each pad. A microcontroller, or similar device, runs a program that puts on the address bus in quick succession all the addresses for the pads that are to be turned on. Each pad is associated with a binary address decoder 830 that recognizes its unique binary address. Upon recognizing its address on the address bus, the particular address decoder turns on a delay/timer, which keeps its output high for the duration of the electrical pulse (that is, the pulsewidth), which, for the main embodiment is 90 microseconds, time set on the delay/timer, which in the main embodiment is fixed in hardware but variations of the main embodiment can have the pulsewidth set in software. The output of said delay/timer turns on an electronic switch, which then connects the particular pad to the voltage (or current) line 211. Once turned on, the pads stay on even after its own address is discontinued from address bus 200 and another address is selected by the microcontroller, staying on for the duration set on the delay/timer 820. The switching from pad to pad, that is, the execution time of the instructions to change the addresses is much faster when compared with the 90 microseconds the pulse lasts in the main embodiment, resulting that all the selected pads will stay on essentially together. Moreover, there is no medical need that the pads must be synchronously active. The microcontroller, which is implanted in other location, usually the chest, contains the battery and all the electrical circuits necessary for the picafina operation. There are voltage or current regulators, which are any of the existing devices, and the same as in current art, and a microcontroller or similar device, which contains a program that runs the innovation of my invention. The microcontroller is capable of receiving instructions via an electromagnetic link from an external programming device here called Doctors Programming Unit (DPU). During a discovery phase, to determine which pads to use, a medically trained operator, using, e.g., a windows-type environment (See FIG. 11) first turns on individual pads or groups of them, also at different voltages (or current) levels, while observing the results, with patient cooperation. After determining the best combination of pads and voltages that suits the particular patient, the medical personnel downloads, from the DPU to the implanted microcontroller, a final program which contains the addresses of all pads that are to be turned on, and the voltages as well, after which a signal is sent to said microcontroller to run the program, which will then periodically send the necessary electrical pulses to the picafina: asserts on the address bus each of the addresses on the list, then stops until 5.56 milliseconds have elapsed (f=180 Hz), then starts the same cycle again. A lengthier explanation of the operation of the invention follows.

OPERATION OF MY INVENTION

Detailed Version

After surgery and patient discharge from the hospital, the patient will schedule several visits to some medical facility (which can be the same facility as the one that made the implant), to program the implanted device. This phase is similar to what is done in current art, except that there are more pads to program in the device of our invention. To program the implanted device the medical practitioner uses electromagnetic or magnetic communication between a unit described further down, called the Doctor's Programming Unit (DPU) and the implanted controlling unit, which is inside the patient, not physically accessible after the surgery is completed and the patient sewed up. Though the implanted device is no longer physically accessible after the surgery, its electrical properties can be adjusted and changed via radio or magnetic or other type of action-at-a-distance communication. Such action-at-a-distance communication is similar to the wireless controls for home electronics, for automobile door opening, for walkie-talkies or cell phones, for wireless network connection, etc. Accordingly, either a general purpose computer with the necessary communication electronics, or else a specially designed computer, are used to send to the implanted unit the necessary parameters and information. Any such device will be here referred to as the Doctor's Programming Unit (DPU), which may contain software for several different types of implanted devices, similarly to a notebook computer containing software for many USB devices, etc. A specially trained medical personnel, as a specialized nurse, or a medical doctor, loads in this Doctor's Programming Unit the software driver that is appropriate for the particular CPU implanted in the particular patient or the appropriate program (driver in software lingo) is loaded automatically as when installing a USB device in any modern computer. This process could be done under a user-friendly windows environment similar to choosing between two word processors, as Word for Windows or WordPerfect, and it can also be that the DPU recognizes which is the model of the patient implanted device, similarly to a computer recognizing any particular USB device and then automatically loads the correct driver. It works similarly to a wireless internet communication with some internet provider, though the technology, frequencies, range, etc are not necessarily the same. The invention is independent of the type of communication link between the external Doctor's Programming Unit (DPU) and the implanted unit that is inside the patient.

There are two phases in the picafina programming: the discovery phase and the final implementation. During the discovery phase the medical practitioner will, by trial and error, find which electrical pads causes the best results for the patients, including absence of side effects, then, after or concomitantly, find also the best voltage values for the best results. An exemplary session could be as follows. The patient arrives at his first session for the discovery phase. The medical practitioner loads the software that is appropriate for the particular unit that is implanted in the patient. This can be done either typing the serial number of the device, or the name of it, or else clicking with the mouse on an appropriate icon, as when loading a word processor, an excel spreadsheet, or other program. This program contains all the necessary intelligence to adjust the implanted device. It contains, among other things, information on the number and position of all pads, as well as on the voltage range possible to chose. The medical practitioner may then start selecting the voltage to use. This could be done, for example, from a software bottom visible on the screen, perhaps marked "voltage level", perhaps on the top of the screen, which, when activated, could offer voltage options to chose from, as when selecting the size of letter on a word processor. Another possibility is the display of a sliding scale, as used to set the volume level when listening to music on the computer, or when using the computer as a telephone. It is also possible to display an empty window, which allows the medical practitioner to type in the voltage value. Any of these and other methods are possible, and may be all offered simultaneously for the medical practitioner to use the one with which he/she is more comfortable. After selecting the voltage level, the medical practitioner will need to choose the pads. When ready to choose the pads, the medical practitioner, still on his/her DPU, may, for example, click on a software bottom, perhaps next to the "voltage level" bottom, indicating "pad choice", or any similar wordings, similar to a bottom that indicates "font types" on a word processing, that typically exists next to the "font size" bottom in most word processors. A drawing may be displayed on the screen, displaying the picafina implanted in the patient. Using a mouse, the medical practitioner selects a pad, say, pad 120_01_01, or a group of pads, say, pads 120_01_01, 120_01_02 and 120_01_03. This step also uses the established conventions, e.g., pressing the "control" key to add pads to the selected list and pressing the "shift" key to select all the pads within a range, which are standard choices used in many word processors, spreadsheets, etc. Upon being selected, the color of this (these) pad(s) on the computer screen may change to confirm its (their) selection, or even a range of colors, each one to code for a different voltage level, or any similar method (colors not shown in figures). Alternatively the medical practitioner may type in the pad addresses he/she wants to select. It is expected that many options will be made available to the user.

For said selection of pads and voltage levels, the medical practitioner will either use a system recommended by the picafina manufacturer, or will use a system developed by him/herself to test variations of pads and voltages that are best for the patient. For example, the discovery session may start selecting all the 12 most distal pads, that is, pads 120_01_01 through 120_01_12 at a low voltage, say 0.5 V. The medical practitioner will then send the information from his/her DPU, via the wireless system, to the implanted unit and then press another software bottom that instructs the implanted unit to start sending the pulses to the picafina. The patient will report the effect, if any. Depending on the effect on the patient, as reported by him/her, and as observed by the medical practitioner, this latter may increase the voltage to 1.0 V and try again, in 0.5 V steps (or any other step) until some effect is reported by the patient or until the maximum allowed is reached, usually near 5 V. This series may be stopped short if undesirable side effects were reported by the patient. At this point, if undesirable side effects were either reported by the patient (say, depression) or observed by the medical practitioner (say, facial pulling), the medical practitioner may try turning on a subset of the pads, say, pads 120_01_01 through 120_01_06. This is the equivalent at the picafina level to selecting a particular angular section of the ring, which physically directs the current onto a particular direction only around the picafina. The medical practitioner will try other combinations too, as indicated by geometry and his/her experience, observing if the undesirable side effects appear or disappear. At this point the medical practitioner will be investigating the current injection towards one side of the picafina, as opposed to all around it. If the undesirable side effect fails to appear when turning on a subset of the pads, then this may be an indication that this set points toward the bulk of the area-of-interest, because it is known that the picafina is often positioned at some edge of the area-of-interest. Next the medical practitioner may use his/her Doctor's Programming Unit (DPU) to turn off all the most distal pads and turn on instead the second next ring of pads towards the proximal end of the picafina, pads numbered 120_02_01 through 120_02_12. He/she will again run the series of allowed voltage levels, increasing the voltage by steps of 0.5 volts, in consultation with the patient, noting all the results, also stopping if undesirable side effects were observed. If undesirable side effects were observed on the most distal set of pads but not when a subset only of pads were turned on, the medical practitioner may then try the same "good" set on this second ring of pads 120_02_xx. This may confirm the previous observation that the picafina is located near the edge of the region-of-interest, with a particular range of pads towards the region-of-interest.

The medical practitioner may then go to ring number 3 (120_03_xx, pads 120_03_01 through 120_03_12), then ring number 4, etc, until the most proximal ring, number 16. Upon completion of this initial series, the medical practitioner may decide to make a more detailed investigation on the effect of some particular pads, depending on the total of reported and observed results, and so on.

Figure 11:
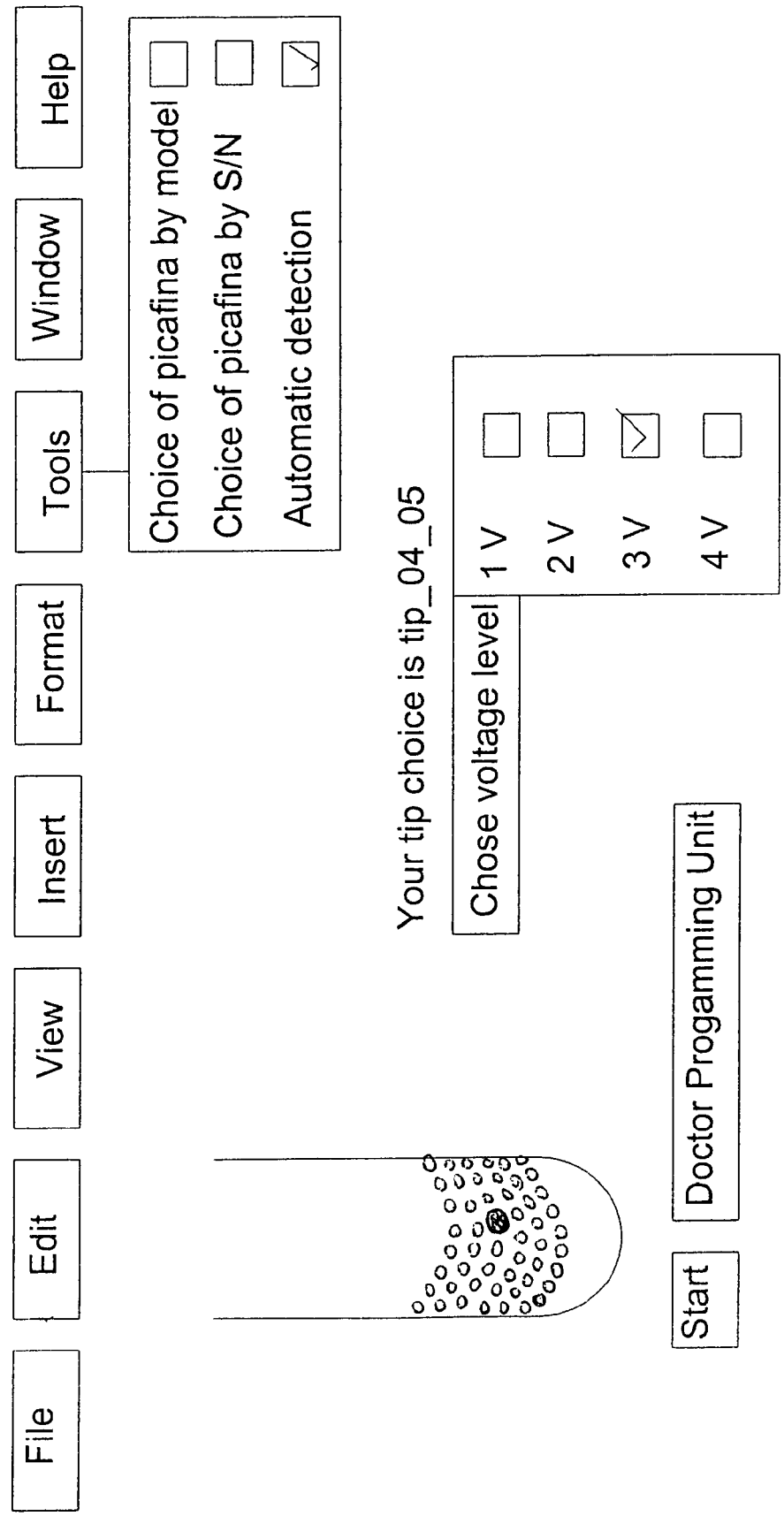
FIG. 11 shows a window environment with the drop-down menus for programming the Doctor's Programming Unit (DPU)

This process may come to completion in one single session or may take more than one session, depending on the patient and on the difficulty of the case. When the discovery process is complete, the medical practitioner will make a complete selection of all the pads that caused the best results, send the information from his/her Doctor's Programming Unit (DPU) to the implanted device and, using another software bottom send an order for the implanted device to keep that sequence running continuously, or during the waking hours only, or every other hour, or some other pattern that is needed. These choices are also available from drop-down menus, similar to choosing line spacing, indentation, etc. on a word processor. FIG. 11 displays a possible window environment for use on this DPU.

Inside the patient the system works as follows. Microcontroller 1200, following the program downloaded by the Doctor's Programming Unit, and after receiving a "go" instruction from said DPU, and as long as it does not receive a countering "stop" instruction from said DPU, asserts on the address bus 200 the address of the first pad on the list created by the DPU, say pad 120_01_01. This being the first pad on the picafina, the address may be, for example, 00000001B=01H=01D (in binary, hex and decimal notation, respectively). At the picafina the address decoder corresponding to the selected pad recognizes the address and set high its output, which in turn starts the timer that keeps its associated output NPN transistor (or switch) on the "on" state for the duration the timer is set, which in this hypothetical case is 90 microseconds. Immediately after, which for a typical microcontroller may be 10 nanoseconds, or 0.01 microseconds, the next address is asserted on the address bus 200, which in this hypothetical case is 00000010B=02H=02D. A different address decoder recognizes this new address, which happens in this case to be next to the previous pad, at the same z coordinate, which then causes its output to go high, which then starts the timer associated with it, which then turns on the NPN transistor that turns the power on to pad 120_01_02, which will then stay on for the same 90 microseconds. Microcontroller 1200 will similarly go through the list of all pads in its memory, one by one, for example: 120_01_01, 120_01_02, 120_02_01, 120_02_02, 120_05_01, 120_05_02. Note that the 10 nanoseconds it takes for microcontroller to move from one address to the next in its list is so short a time when compared with the 90 microseconds each pad is on, that it can be considered instantaneous. After the last pad is turned on, microcontroller 1200 will put on the address bus 200 a non-existing address, say 00000000B, so as no pad is set on until next cycle starts, which takes 5.55 milliseconds (f=180 Hz) from the beginning of the cycle, after which time a new cycle starts again with the first address in the list, pad 120_01_01, which is 00000001B, and so on. The result of the process is that every 5.55 milliseconds (that is, at a frequency f=180 Hz) the full set of selected pads is set at the correct voltage, injecting the current at the appropriate places for the desired duration of 90 microseconds.

Several necessary appurtenances to the microcontroller 1200 and current controller 1230 (not shown) in box 1200 (not shown), and to the address decoder 830, timer/delay 820 and electronic switch 810 inside the picafina are not mentioned because they are common elements known to professionals with current knowledge in the art of electronics. For example, there ought to exist a crystal controlled oscillator to keep the time (that is why all computers wake-up with the correct time-of-the-day+date); this and other known appurtenances are omitted in my description of the device.

Figure 13C:
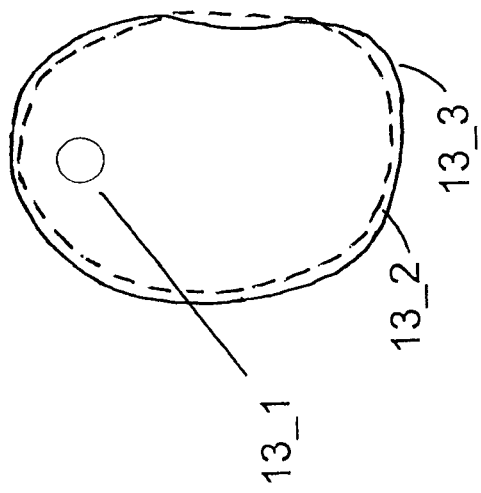
FIGS. 13a and 13b show two possibilities of electrical current reaching less (a) and more (b) then the target volume using current art technology, while FIG. 13c show the result on the current reach of different voltage levels on the pads.
Figure 13B:
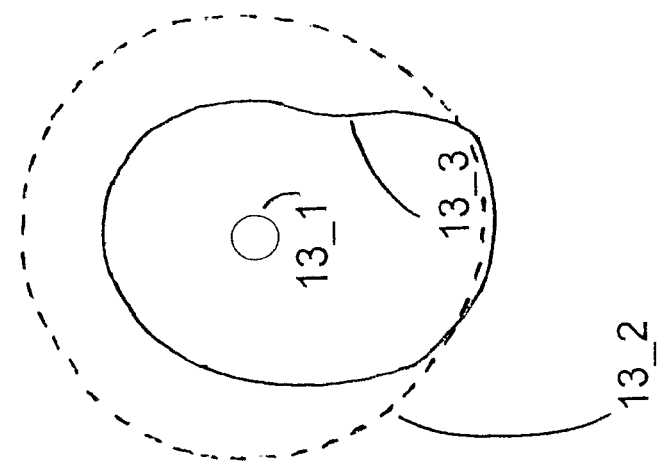
Figure 13A:
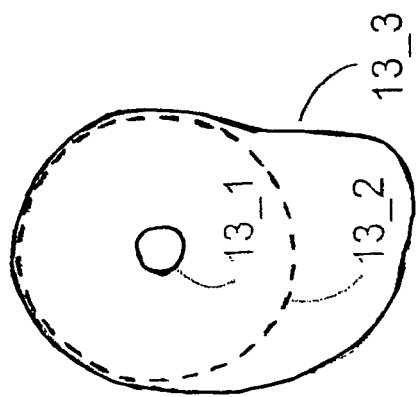

FIGS. 13a and 13b show two possibilities of electrical current reaching less (a) and more (b) then the target volume using current art technology, while FIG. 13c show the result on the current reach of different voltage levels on the pads. This simple description is well known in physics and electronics by the name of field-shaping, which is more complex than this representation here, and is a well-known effect which can be used to achieve better results only with the larger and individually controlled pads of our invention. Referring to FIG. 13c for a concrete case study, with the picafina positioned by the surgeon as indicated, and remembering that the surgeon has no means to position the picafina at the center of the region of interest, the stimulation pads number 1, 2, 3, 4 and 5 should be energized, while pads 6 through 12 should be left un-energized or energized at a lower voltage or current. This choice, in this case, is dictated by these pads being the ones that would cause an electrical current to flow through the region of interest indicated, while causing none or minimal current outside such region of interest. In practice the medical personnel does not know where the picafina is located with respect to the region of interest, that is the person that is adjusting the picafina for optimal performance, does not know what is displayed in FIG. 10c. So this choice is not made based on the unknown position, but rather on observing good results, bad results or indifferent results. The choice is made by observing the existence of side effects, that would occur when energizing any of the pads 6 through 12, and also observing the alleviation of the Parkinson Disease symptoms when energizing pads 1 through 5. In other words, the choice is made from the observation of the effects, not from an a priori knowledge of the positioning, as suggested by 13c, which is only draw for purposes of understanding the functioning. Also, depending on the size of the region of interest, more or less layers of pads would be energized, all above and below said pads 1 through 5. Let us assume, for simplicity, that only two layers are to be energized in a picafina positioned as indicated in FIG. 13c. The reader is reminded again that the actual position is never known, as in 13c, but rather the results of stimulation are known, from which it is determined which pads to activate. The following pads would be then energized: 01__1 through 01_05, 02_01 through 02_05, etc.

It is better to describe the functioning of the picafina of my invention by comparing it to the prior art. Prior art picafina is generally unable to avoid injecting current on the side of pads 6 to 12 in FIG. 13c, this being a possible reason for the known side effects of DBS.

FIGS. 13a and 13b display two other possible relative relations between the picafina inserted in a brain and a particular area of interest. The situation depicted in FIG. 13a would cause under stimulation, while the situation depicted in FIG. 13b would cause over-stimulation with possible side effects. Neither is desirable. A picafina which were able to adjust the voltage values at arbitrary points on its surface could ameliorate this situation.

DESCRIPTION AND OPERATION OF ALTERNATIVE EMBODIMENTS

Second Embodiment of My Invention

Description of the Invention

Description of Second Embodiment

Short, Electrical Engineering Version

Figure 8B:
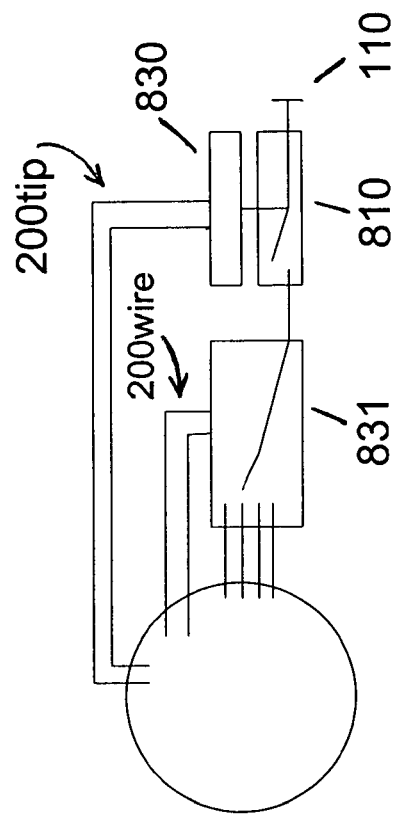

A second embodiment discloses the use of multiple voltage (or current) wires (211) to set the stimulating electrical pads at different voltage (or current) values as needed, and a separate second binary address bus (201) to select which of said wires is connected to said stimulating pads (110_xx_yy). Said second binary address bus (201) is separate from the first digital addressing system only logically, as each is an independent set of wires running in parallel, with the same function though using separate wires each. It is also possible to use the same set of wires then a separate switch to select what is being addressed, the pads or the current carrying wires. Each of the available wires 211 to carry the stimulating signal can be connected to any of the available stimulating pads 110, allowing several simultaneous different voltage (or current) settings, as many as there are stimulating wires 211. For the benefit of the medically-oriented reader, not familiar with electronics terminology, we define here what is known in electronics as a demultiplexer. A demultiplexer is a type of electronic switch with a single input and a plurality of outputs, also with a number of binary inputs capable of creating a binary address which can select which of the outputs will be connected to the single input (cf. multiplexer). The device of our invention uses a demultiplexer capable of also latching the output selection, that is, a demultiplexer that maintain the connection between the single input and the selected output even after the address is out from its address port (it latches), or even if the address changes to another value. In this embodiment at the same time that a stimulating pad is selected, the output of its address decoder 830 besides opening (on) the electronic switch associated with the pad that corresponds to itself, also enable said second address decoder 831 (or a demultiplexer) that selects one of the signal carrying wires 211 to connect the selected measuring pad to one of the available stimulating wires 211—the one selected by said second address decoder 831 according to said second address bus 201 (see FIG. 8*b*). FIGS. 8*a* and 8*b* show one of the possible implementations of the electronics used for the alternative embodiment of our invention using several measuring pads and several signal carrying wires, including the switches to select the pads and the demultiplexers to select the signal carrying wires. These two figures are an extension of FIGS. 7*a* and 7*b*, with the added possibility of multiple current carrying wires to set the electrode pads at different voltage levels and/of at different time patterns. FIG. 8*b* shows a detailed block diagram of a possible electrical connection of one electrical pad of the picafina of our invention. This is a exemplary system, others being possible. In FIG. 8*b* many details are either omitted or else indicated as a possible option that in any particular implementation may be different to suit the particular electronics details. For example, the enable signal to said second address decoder 831, which in FIG. 8*b* is taken as the output of said first address decoder 830, could be pulse stretched if needed to meet timing specifications of said second address decoder 831. Such details are obvious to the practitioners of the art and are not indicated in this patent description. It is intended that the number of connecting wires is much smaller than the number of stimulating pads, or the order of 10 s stimulating wires against an order of several thousands stimulating pads, but this is not limiting to my invention. Once the address for a particular connecting wire is selected, this address is latched, freeing both address buses to assert other addresses.

Description of Second Embodiment

Detailed Version

The second embodiment of my invention uses two address buses, 200 to select which stimulating pads is on, and 201 to select a particular wire which sets the voltage (or current) level. This alternative embodiment offers the possibility of having several separate wires 211 connecting any stimulating pad 110 to one of a plurality of wires 211 setting different voltage (or current) values. In this embodiment the number of stimulating pads is still very large, say a few thousands, with a smaller number of connecting wires, say one to a few dozens or even less than a dozen. In this embodiment, after (or concomitantly) selecting a particular stimulating pad 110 with decoder 830, say 120_10_01, the user sets another address in another independent address bus 201, which is decoded by another address decoder 831 (FIGS. 8*a* and 8*b*), which selects a particular connecting wire 211 to set the voltage (or current) at stimulating pad 120_10_01 to one of the possible values, each of said possible values being available at one of the voltage (or current) wires 211. In this embodiment there is a holding memory (or latch) associated with address decoder 830 because the stimulating pad and the connecting wire have to stay selected even after the address buses 200 and 201 have other address values for other combinations.

Consequently this second embodiment of my invention extends the use of the stimulating system to the selection of one connecting voltage (or current) wire from a plurality of wires available throughout the body of the picafina, each one capable of connecting any of the stimulating pads with the proximal end of the picafina of my invention, from which they can be extended by ordinary means to the power supply capable of producing a plurality of voltages (currents). FIG. 8*a* shows the electronic connections and parts. Stimulating pad 110 is connected via a first digitally controlled switch 810, which turns on/off under the control of a first address decoder 830, to said second address decoder 831, which connects said stimulating pad 110 to one of the wires 211, each one set at a different voltage (or current) level. Once the address bus selects an address for the voltage (current) wire 211_zz the selection is latched and stay latched until a signal is send to another wire, not shown, which has the appropriate circuitry to unlatch all the latched addresses, which can be used to select new stimulating pads and new connecting wires with a new selection cycle. The address bus that selects an address for the stimulating pad 110_xx_yy has a timer/delay circuit as in the main embodiment, which causes that the stimulation once chosen stays on for a set time even after a new address is set on the stimulating address bus. Second embodiment of my invention. Operation of the second embodiment.

To operate the second embodiment the user must start resetting all the latches to the off state, which he/she does with the latch off signal at wire_latch (not shown). He/she then starts selecting the first address for the stimulating pad with address decoder 830 he/she needs in the same way as is done with the main embodiment, e.g., with individually set switches, or with a decoding pad, or with a microcomputer or any equivalent way as known to the practitioners of the art, then, at the same time (concomitantly) the user also selects the address for one of the available connecting wires 211_zz which run inside the length of the picafina of my invention, which carries the voltage (current) that he/she wants to use on said particular stimulating pad. Both addresses (200 and 201) have to be selected concomitantly because in this second embodiment the address decoder 830 that selects a particular surface measuring pad also enables said second address decoder 831 that selects which voltage (current) wire 211 is chosen, so that the power (voltage or current) wire is connected only to the selected stimulating pad. With this the user has completed the connection from the selected stimulating pad to a single, identifiable wire at the proximal end of the picafina of my invention. The user selects then a second stimulating pad 110 and a second connecting wire 211 in the same manner as the previous one, then a third and so on, until he/she selected all the desired stimulating pads using one of the available power wires (voltage or current) for each stimulating pad. Note that the voltages selected for each stimulating pad 110 may or may not be different from each other—the option is available if needed but inspection of the connections described and indicated in the drawings will show that said pads can be all set at the same voltage (or current). When all the stimulating pads selections are made and the connecting wires 211 have been connected to the external power source according to the desired voltage (or current) in each stimulating pad, the stimulating system is ready for a go signal to keep running as programmed by the medical practitioner. Several voltage (current) values can be used in parallel with this second embodiment, for example, to stimulating areas of different sizes or of different impedances.

Third Embodiment of My Invention

Description of the Invention

Description of Second Embodiment

Short, Electrical Engineering Version

A third embodiment of my invention is the extension of said second embodiment using some of the power (voltage) wires as signal measuring wires. In this embodiment some of the wires 211 that set different voltages for said pads 110 are use as disclosed in said second embodiment, connected to a battery or other voltage (or current) source, while some of said wires 211 are connected to a voltmeter or some other measuring instrument. In this third embodiment the picafina of my invention is used not only to put a current on some neurons (stimulation) but to make measurements of the voltages at other neurons as well. Typically these two functions are separate but there is no reason to be so other than the prior art impossibility to have enough pads available for both. In this third embodiment said switch 810 is designed with an imput to latch its on-state (not shown), so as the measurements can be continuously made once said switch 810 is selected. Instead of a latch on said switch 810 other possibilities exist, as know to the practitioners of the art of electronics engineering.

Still another alternative embodiment of my invention is the use of radio signals to create the addresses for the first address decoders (address decoders for the stimulating pads). In this embodiment there is no physical first address wires connecting the distal end of the picafina with the user (researcher or neurologist). Any radio communication link is feasible, over the EM spectrum, including, e.g., radio waves of all frequencies and wavelengths, microwaves, infrared, visible, ultraviolet etc., and such action-at-a-distance information is sometimes referred to as telemetry. This invention does not include a new radio communication system, but simply use existing telemetry devices. In this alternative embodiment the connecting wires for the first address bus 200 are substituted by a telemetry unit inside the picafina of my invention, which receives the addresses sent by the user using a transmitting unit. Once received, the addresses are stored in memory physically located at the distal end of the picafina, near the measuring tips, said storing memory taking the place of the connecting wires. Such an alternative embodiment decreases the number of wires connecting the picafina with the outside world, which may be important when taking measurements on small animals, as in a mouse or even on an insect, when it may be advantageous to use smaller wires connecting the animal to the controlling and measuring instruments.

Still another alternative embodiment of my invention is the use of radio signals to create the addresses for the second address decoders (address decoders for the power wires—voltage or current). In this embodiment there is no physical second address wires connecting the distal end of the picafina with the user (researcher or neurologist). Any radio communication link is feasible, over the EM spectrum, including, e.g., radio waves of all frequencies and wavelengths, microwaves, infrared, visible, ultraviolet etc., and such action-at-a-distance information is sometimes referred to as telemetry. This invention does not include a new radio communication system, but simply use existing telemetry devices. In this alternative embodiment the connecting wires for the address bus 201 are substituted by a telemetry unit inside the picafina of my invention, which receives the addresses sent by the user using a transmitting unit. Once received, the addresses are stored in memory physically located at the distal end of the picafina, near the measuring tips, said storing memory taking the place of the connecting wires. Such an alternative embodiment decreases the number of wires connecting the picafina with the outside world, which may be important when taking measurements on small animals, as in a mouse or even on an insect, when it may be advantageous to use smaller wires connecting the animal to the controlling and measuring instruments.

Still another alternative embodiment of my invention is the use of radio signals to create the addresses for both the first and the second address decoders (address decoders for the stimulating pads and address decoders for the power wires—voltage or current). In this embodiment there is no physical first and second address wires connecting the distal end of the picafina with the user (researcher or neurologist), both advantages mentioned on the two paragraphs above being attained simultaneously.

CONCLUSION, RAMIFICATIONS, AND SCOPE OF INVENTION

It ought to be obvious to people skilled in the art that far more independent stimulating pads or contacts are possible to address in the form disclosed in the main embodiment, which is presented with 12 pads per ring and 16 rings, only to make it easier to follow the drawings and explanation.

The connections inside said picafina are made with any of the technologies developed for printed circuits and/or chip manufacture (integrated circuits or IC). As used here, the term "integrated circuit" refers to a small-scale electronic device, densely packaged with more than one integrated, electrical component. The components are manufactured on the surface of semiconductor material. There are various scales of integrated circuits that are classified based on the number of components per surface area of the semiconductor material, including small-scale integration (SSI), medium-scale integration (MSI), large-scale integration (LSI), very large-scale integration (VLSI), ultra large-scale integration (ULSI). For example, both the subtractive and the additive processes used in printed circuit manufacture can be used to print the connecting power and address lines. The integrated circuits and transistors shown, for example, at figure FIG. 7 could be made with the ordinary technology used for chip manufacture, as well as some of the wires that interconnect them and/or wires that connect them with the main connecting wires along the picafina. It is also possible to use a combination of these, some connections using the printed circuit technology, other using the smaller IC technology, the particular choice depending on the size and complexity of the particular picafina.

Thus the reader will see that the electrode pads of the invention provide a highly reliable device which offers the advantage over prior art of being able to deliver electrical pulses on more precisely located points on the vicinity of neurons, nerves and other cells inside living organisms than prior art does. The smaller dimensions of the delivering electrodes (pads) of my invention allow for more precise delivery of current to a single neuron, if so desired, instead of average distributed shotguns to very many neurons that happen to be near a larger delivering probes of prior art. At the same time my invention permits the delivery of electrical pulses from many pads in parallel, which pads can be adjoining to each other, making the equivalent of a larger pad of prior art, or from spatially separated pads, allowing for new and unexpected results. These options give more flexibility and options to the user of my invention. Moreover, the electrode pads of my invention allow for changing the position of pulse delivery from points separated by a few micrometers, or the distance between each pad, without moving the supporting structure (the picafina). This possibility of changing the delivery pad to be used while keeping the picafina of my invention in the same place is important, as each repositioning involves trauma to the animal. Moreover, the change from one pad to the other is also important, because the distance between the pads can be made very small, a few micrometers with modern technology of semiconductor and printed circuit board (PCB) manufacture, which is much smaller than the separation between pads in multi pad stimulating devices in used today by current art. Though the picafina cannot be positioned with any accuracy with respect to any neuron or other body cell, the possibility of adjustments of the delivery position, switching from one pad to another nearby pad is equivalent to micropositioning the delivery site, or to make small changes on the pulse delivery site.

Another improvement is in making neural stimulations that advance spatially on time along the neurons, which can be achieved by turning the small pads on as a progressive wave that passes by, turning off the pads behind, as the letters on announcement displays that moves the letters, or as the lighted pointing arrows ordering lane changes on highways at construction sites, a possibility that can potentially open the possibility of a less intrusive neural stimulation (not as much current, not as much electrical power), also more localized in area (that is, volume), sparing unnecessary neurons from being stimulated.

The wires at the proximal end of the picafina of my invention do not have to be grouped as indicated in the main embodiment, any other grouping being acceptable, as the grouping does not alter the working of my invention. For example, all the wires could end on a single connector, or each wire could have its own dedicated connector, or any combination of these, because the particular form of connecting the wires are not part of this invention.

The wires or cables at the proximal end of the picafina of my invention may be duplicated (redundant wires), as shown at FIG. 12, so that the picafina of my invention can still be used if one of the wires happens to break, simply changing to its backup wire or cable.

Figure 5A:
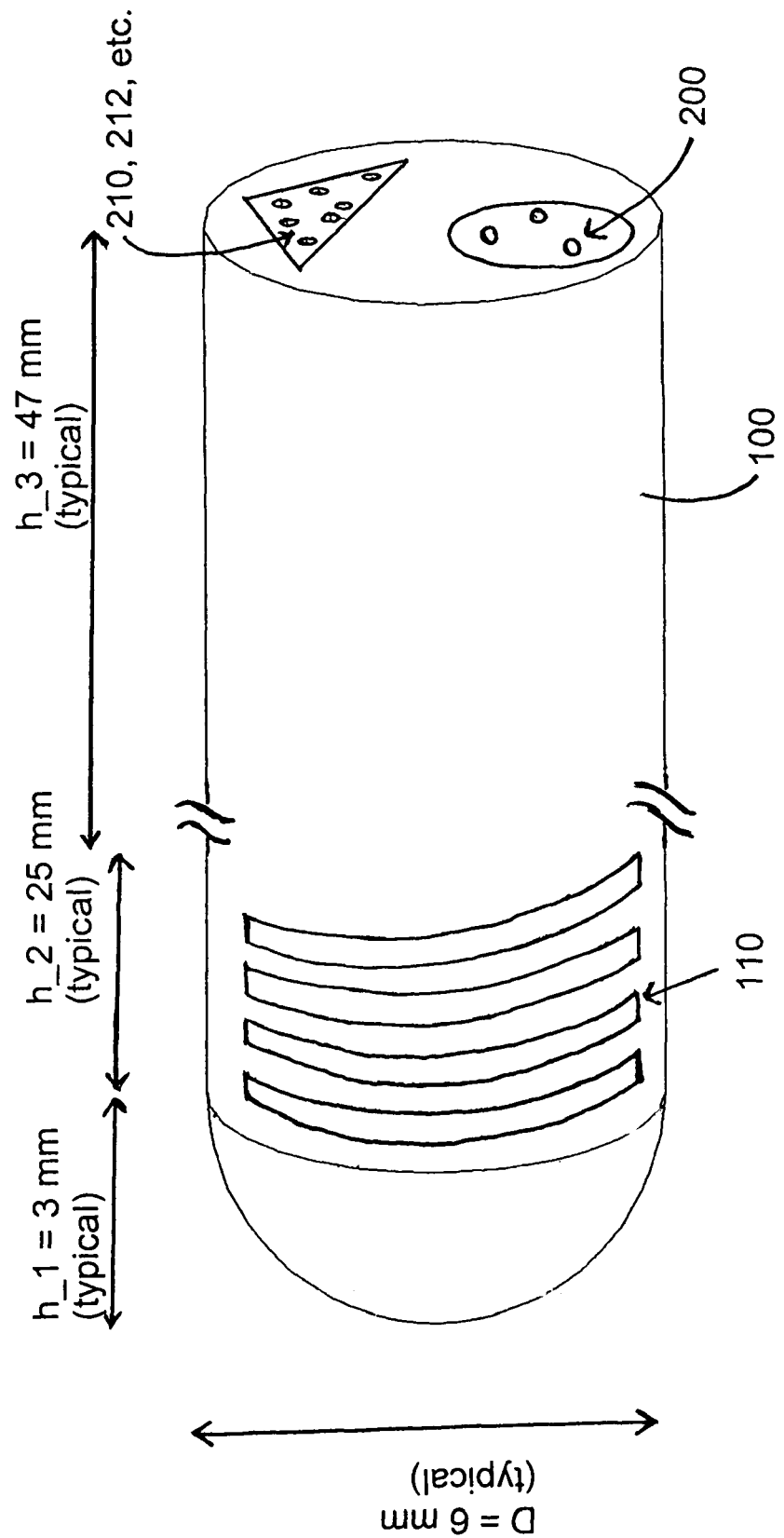
FIGS. 5a and 5b show variations on current art of picafina that can be implemented with existing technologies that allow a small number of electrical contacts.
Figure 5B:
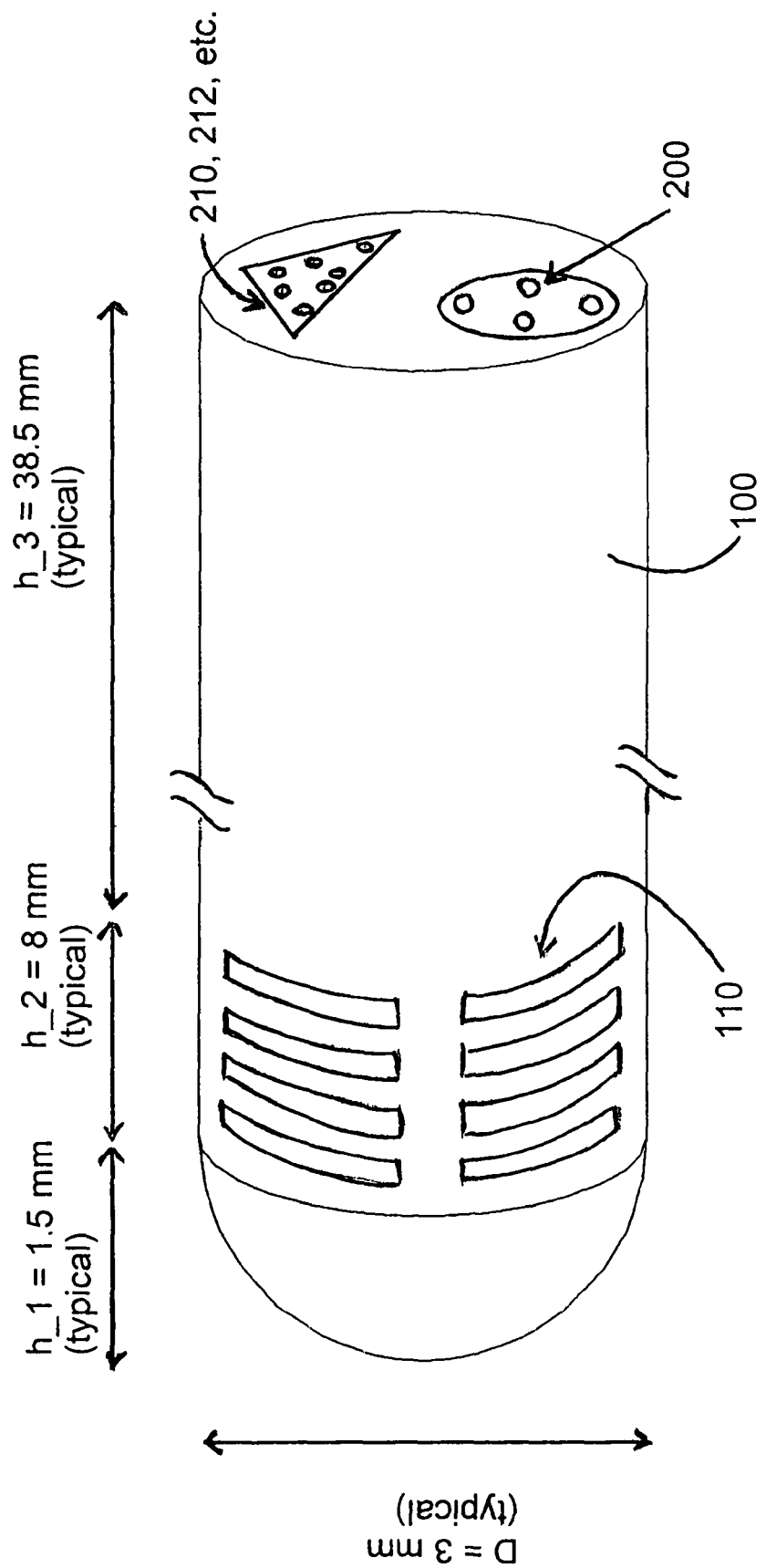

The pulse delivery pads can be of any shape different of the circular shape indicated in the main embodiment without altering the scope of the invention. For example, the delivery pads can be square shaped, as indicated in FIG. 2, or they can be elongated, as shown at FIG. 3, or they can be in the shapes shown at FIGS. 5a and 5b. These variations and many others are possible and fit particular applications, none of them expressing any intrinsic variation from my invention.

Figure 6A:
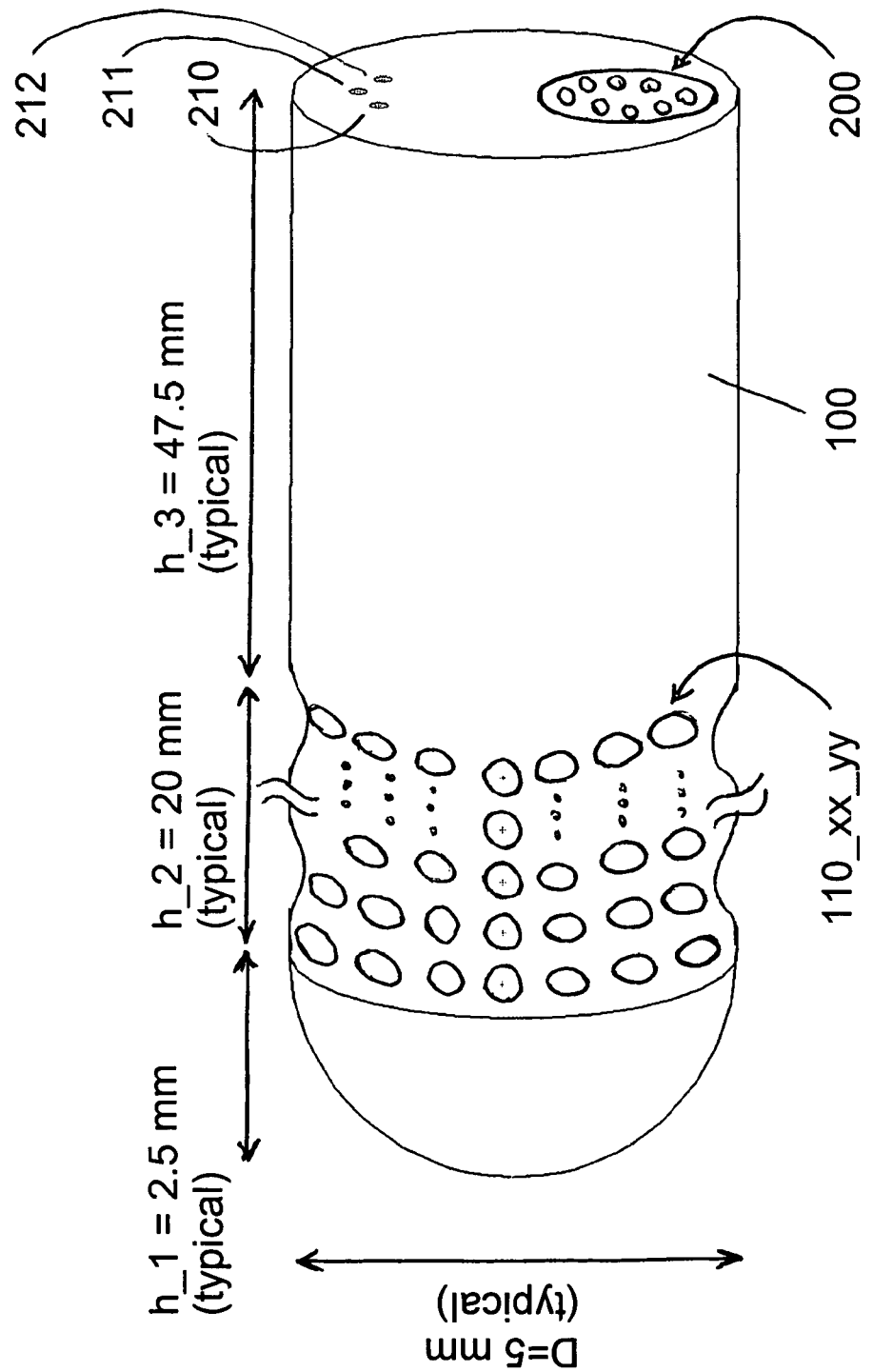
FIGS. 6a and 6b show two alternate profiles for the picafina.
Figure 6B:
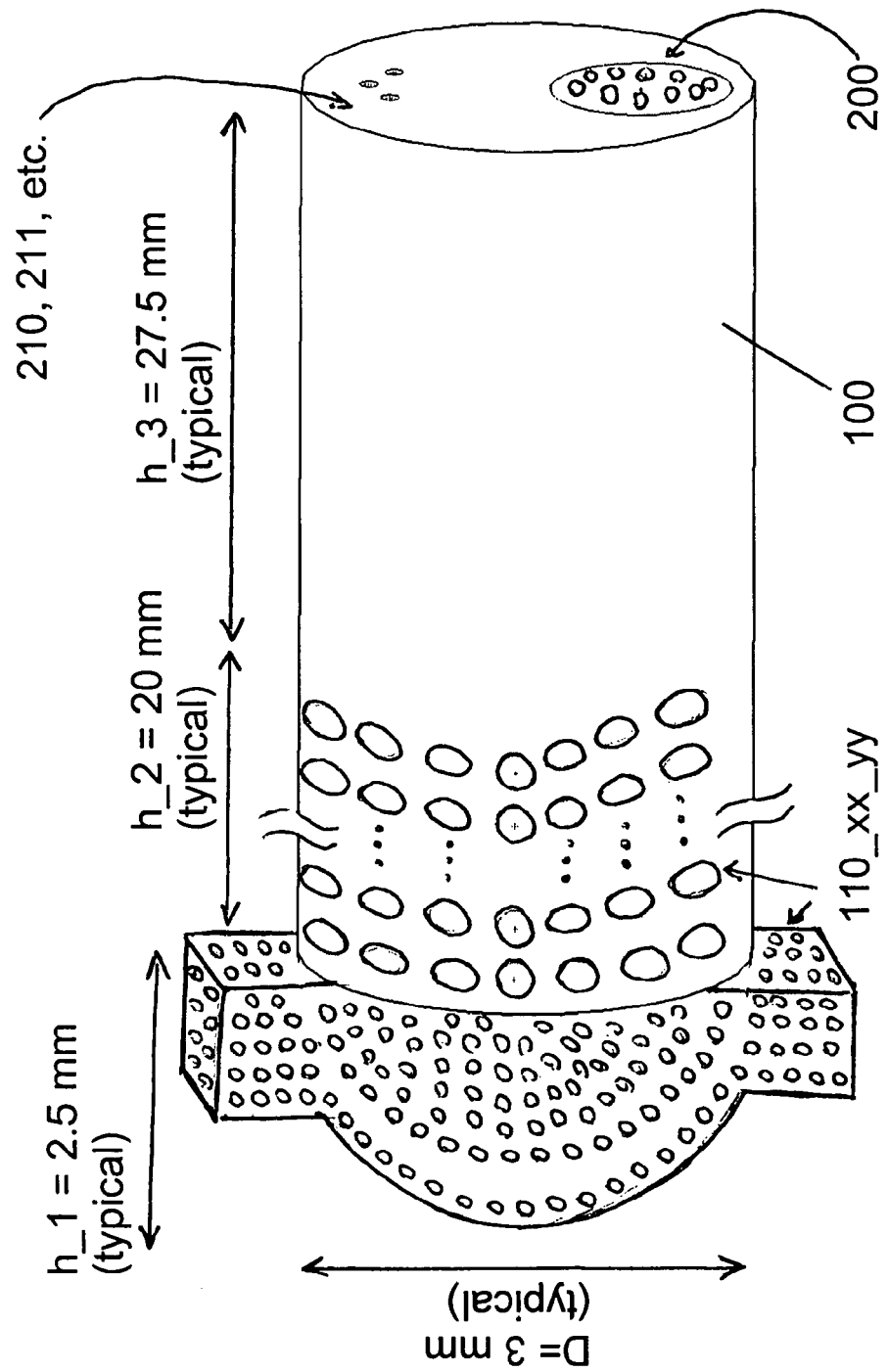

The very body of the picafina of my invention can have shapes other than cylindrical. FIGS. 6a and 6b show two such possible variations. Variations on the shape of the picafina of my invention to adapt to specific applications do not constitute an intrinsic variation of my invention and are covered by this patent.

The distal interior part of the picafina described in the main embodiment is solid and made of the same material as its surface, but this is not necessary, it being possible to have a hollow interior, or an interior made of a different material then the exterior surface, this detail not affecting the working of the invention as it will be seen by the persons familiar with the art.

The address decoders 830 that turn on/off the switches 810, thereby connecting the pulse delivering pads 110 can be as simple as a digital (or binary) comparator, for example the National Instruments 54AC520 or the Texas Instruments 5962-8681801RA, or some other more complex circuit, or even a especially designed electronic circuit, the particular nature of the address decoder not impacting my invention, but only that it recognizes that the address asserted in the address bus 200 is the same as the address assigned to the contact that it is supposed to turn on/off.

While my above description contains many specificities, these should not be construed as limitations on the scope of the invention, but rather as an exemplification of one preferred embodiment thereof and a few typical variations. Many other variations are possible. For example the cross section of the picafina of my invention can be of many other shape, as elliptical or rectangular. Besides elliptical and rectangular, it can be of any irregular shape, or the cross section can even vary along the long dimension of the picafina. The pulse delivering pads do not have to be flush with the picafina's body, but can be either protruding out of it or be recessed onto it. The dimensions suggested for the main embodiment are intended for a picafina designed to deliver electrical pulses deep in the brain of a human animal; these dimensions are necessarily different when the intended animal is not a Homo, as a smaller mouse or an even much smaller insect, or for stimulation at the brain cortex, for example, which is located just below the skull, or for stimulation on the spinal cord, or from other neurons or other cells on the heart, intestines, or any other organs or extremities like arms. The stimulating pads can be made of metals other than titanium, such as platinum, vanadium, iridium, silver, gold, surgical steel, stainless steel, MP35N, platinum-iridium, amalgams, alloys, and combinations, among others. and the body can be made of other insulators other than silicone, such as polyurethane, polyethylene, polyimide, polyvinylchloride, PTFE, ETFE, ceramics, various biocompatible polymers, or combinations of these, among others.

The connections inside said picafina are made with any of the technologies developed for printed circuits and/or chip manufacture (integrated circuits or IC). For example, both the subtractive and the additive processes used in printed circuit manufacture can be used to print the connecting power, ground and address lines. The integrated circuits and transistors shown schematically, for example, at FIGS. 7a and 7b, could be made with the ordinary technology used for chip manufacture, as well as some of the wires that interconnect them and/or wires that connect them with the main connecting wires along the picafina. It is also possible to use a combination of these, some connections using the printed circuit technology, other using the smaller IC technology, the particular choice depending on the size and complexity of the particular picafina.

Accordingly, the scope of the invention should be determined not by the embodiment(s) illustrated, but by the appended claims, drawings and invention description, and their legal equivalents, including obvious extensions and variations of it as seen by persons with normal skills in the art.

The invention claimed is:

1. A method of increasing the reliability of an electrical connection between a first group of elements composed of an electrode array at a first location with at least one electrode connected to a first group of wires composed of at least one wire, and a second group of elements composed of an energy storage unit and a controlling electronics at a second location connected to a second group of wires composed of at least one wire, the method comprising:
   providing a first electrical connector with male and female matching pair which is capable of connecting the first group of wires connected to the electrode array to the second group of wires connected to the electrical energy storage unit and the controlling electronics;
   providing a second redundant electrical connector with male and female matching pair which is capable of duplicating at least one of the connections provided by the first electrical connector;
   wherein the electrodes are configured to inject electrical currents on the cells surrounding the electrodes or to act as measuring points for measurements of the electrical environment on the cells surrounding the electrodes;
   wherein the second redundant electrical connector with male and female matching pair provides for a back-up connection at the connection point between the first group of wires and the second group of wires, the redundant connector with male and female matching pair being configured to maintain the electrical connection between the first group of wires and the second group of wires in case the at least one of the connections with redundancy fails.

2. The method according to claim 1, further providing at least one redundant wire in parallel connection with at least one wire of the second group of wires leading from the at least one of the connections with male and female matching pair at the second redundant electrical connector to the electric energy storage unit and the controlling electronics;
   wherein the at least one redundant wire is capable of providing an alternative connection between the redundant electrical connector with male and female matching pair and the energy storage unit and control electronics, thereby maintaining the electrical connection between the electrodes and the energy storage unit and control electronics, in case of one of the wires with redundancy fails.

3. The method according to claim 1, wherein the first group of wires leading to the electrodes and the second group of wires leading to the energy storage unit and to the controlling electronics belong to at least one of a group of power wires, a group of measurement wires, a group of return wires, a group of digital addresses wires and a group of digital control wires;
   wherein the power wires are at different voltage levels or different current levels and configured to cause a different effect on cells surrounding the electrodes;
   wherein the measurement wires are configured to transfer information measured by the electrodes configured to act as measuring electrodes;
   wherein the return wires are configured as return for the electrical currents on at least one of the wires;
   wherein the address wires are configured to transfer binary address information;
   wherein the control wires are configured to transfer control information.

4. The method according to claim 1, wherein all the address-type connections at the first electrical connector with male and female matching pair are duplicated at the second redundant electrical connector with male and female matching pair, whereby all the address connections between the first group and the second group have a back-up duplication to keep the electrical connection in case of connection failure.

5. The method according to claim 1, wherein all the electric power-type connections at the first electrical connector with male and female matching pair are duplicated at the second redundant electrical connector with male and female matching pair, whereby all the electric power connections between the first group and the second group have a back-up duplication to keep the electrical power connection in case of connection failure.

6. The method according to claim 1, wherein all the connections at the first electrical connector with male and female matching pair are duplicated at the second redundant electrical connector with male and female matching pair, whereby all the connections between the first location and the second location have a back-up duplication to keep the electrical connection in case of connection failure.

7. The method according to claim 2, wherein all the second group of wires is duplicated, creating a complete redundant connection for all the second group of wires from the electrical connectors to the electric energy storage unit and controlling electronics at the second location.

8. The method according to claim 1, wherein the electrode array is composed of a first group of electrodes used for electrical stimulation of tissues surrounding the electrodes, and a second group of electrodes for measurements of the electrical activity on tissues surrounding the electrodes;
   wherein the measurements are capable of providing information to the electronics controlling unit that allows for selecting of an optimized electrical stimulation.

* * * * *